United States Patent
You et al.

(10) Patent No.: US 10,342,513 B2
(45) Date of Patent: Jul. 9, 2019

(54) MEDICAL DIAGNOSTIC APPARATUS CAPABLE TO OPERATE BETWEEN STORED OPERATING STATES AND OPERATING METHOD THEREOF

(71) Applicant: SAMSUNG MEDISON CO., LTD., Gangwon-do (KR)

(72) Inventors: Young-kwon You, Gangwon-do (KR); Jun-kyo Lee, Gangwon-do (KR); Sung-yoon Kim, Gangwon-do (KR); Gil-ju Jin, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 1020 days.

(21) Appl. No.: 14/657,869

(22) Filed: Mar. 13, 2015

(65) Prior Publication Data
US 2015/0257737 A1   Sep. 17, 2015

(30) Foreign Application Priority Data

Mar. 13, 2014   (KR) .......................... 10-2014-0029765

(51) Int. Cl.
*A61B 8/00*   (2006.01)
*A61B 8/08*   (2006.01)
(Continued)

(52) U.S. Cl.
CPC ............ *A61B 8/463* (2013.01); *A61B 5/4836* (2013.01); *A61B 8/465* (2013.01); *A61B 8/467* (2013.01);
(Continued)

(58) Field of Classification Search
CPC .... A61B 2560/0475; A61B 2560/0487; A61B 2576/00; A61B 5/4836; A61B 5/7475;
(Continued)

(56) References Cited

U.S. PATENT DOCUMENTS 5,997,478 A * 12/1999 Jackson ................... A61B 8/00
                                                                  600/437
6,238,341 B1   5/2001 Mullen
(Continued)

FOREIGN PATENT DOCUMENTS

EP      2145580 A1    1/2010
JP   2007-296079 A   11/2007
(Continued)

OTHER PUBLICATIONS

International Search Report dated Mar. 31, 2015, issued in corresponding International Patent Application No. PCT/KR2015/000106.
(Continued)

*Primary Examiner* — Michael T Rozanski
(74) *Attorney, Agent, or Firm* — Morgan Lewis & Bockius LLP

(57) ABSTRACT

Provided is a method of operating a medical diagnostic apparatus that displays a medical image, including: modifying an operating state of the medical diagnostic apparatus from a first state to a second state based on sequential first user inputs; storing a history of a plurality of operating states respectively corresponding to the first user inputs; receiving a recovery input; selecting a third state from among the plurality of operating state included in the history, based on the recovery input; and modifying the operating state of the medical diagnostic apparatus from the second state to the third state.

20 Claims, 17 Drawing Sheets

(51) Int. Cl.
*A61B 5/00* (2006.01)
*A61B 6/00* (2006.01)

(52) U.S. Cl.
CPC ............. *A61B 5/7475* (2013.01); *A61B 6/465* (2013.01); *A61B 8/0866* (2013.01); *A61B 2560/0475* (2013.01); *A61B 2560/0487* (2013.01); *A61B 2576/00* (2013.01)

(58) Field of Classification Search
CPC ....... A61B 6/465; A61B 8/0866; A61B 8/463; A61B 8/465; A61B 8/467
See application file for complete search history.

(56) References Cited

U.S. PATENT DOCUMENTS

| | | | |
|---|---|---|---|
| 6,370,413 B1 * | 4/2002 | Alvarez | A61B 8/00 600/437 |
| 6,475,146 B1 | 11/2002 | Frelburger et al. | |
| 6,904,161 B1 | 6/2005 | Becker et al. | |
| 2004/0111028 A1 * | 6/2004 | Abe | A61B 8/463 600/437 |
| 2010/0010345 A1 * | 1/2010 | Shin | A61B 8/00 600/437 |
| 2010/0023886 A1 | 1/2010 | Shin et al. | |
| 2010/0145195 A1 | 6/2010 | Hyun | |
| 2011/0137836 A1 * | 6/2011 | Kuriyama | A61B 5/1118 706/12 |
| 2013/0012817 A1 | 1/2013 | Ahn | |
| 2013/0058533 A1 | 3/2013 | Ren et al. | |
| 2013/0296707 A1 | 11/2013 | Anthony et al. | |

FOREIGN PATENT DOCUMENTS

| | | |
|---|---|---|
| JP | 2010-274049 A | 12/2010 |
| KR | 10-1999-0084449 A | 12/1999 |
| KR | 10-2010-0011669 A | 2/2010 |
| KR | 10-2012-0110480 A | 10/2012 |
| KR | 10-2013-0004854 A | 1/2013 |

OTHER PUBLICATIONS

Extended European Search Report dated Oct. 23, 2017 issued in European Patent Application No. 15761364.7.

* cited by examiner

FIG. 8A

| Color | | | | |
|---|---|---|---|---|
| Frequency : | ☐ Res. | ☑ Gen. | ☑ Pen. | }821 |
| Steer : | ☐ Left | ☑ None | ☐ Right | }822 |
| Blending Level : | 0%  24% | | 100% | }823 |
| Filter : | 0 | 1 | 3 | }824 |
| Balance : | 0 | | 24   31 | }825 |

| Color | | | | |
|---|---|---|---|---|
| Frequency : | ☐ Res. | ☑ Gen. | ☐ Pen. | }821 |
| Steer : | ☐ Left | ☐ None | ☑ Right | }822 |
| Blending Level : | 0% | | 100% | }823 |
| Filter : | 0 | | 3 | }824 |
| Balance : | 0 | 15 | 31 | }825 |

| Color | | | | |
|---|---|---|---|---|
| Frequency : | ☐ Res. | ☑ Gen. | ☐ Pen. | }821 |
| Steer : | ☐ Left | ☐ None | ☑ Right | }822 |
| Blending Level : | 0% ━━━━━━━━━━ 100% | | | }823 |
| Filter : | 0 ▓▓▓▓▓▓▓▓▓▓ 3 | | | }824 |
| Balance : | 0 ▓▓▓▓▓▓ 18 ━━ 31 | | | }825 |

820

MEDICAL DIAGNOSTIC APPARATUS CAPABLE TO OPERATE BETWEEN STORED OPERATING STATES AND OPERATING METHOD THEREOF

RELATED APPLICATION

This application claims the benefit of Korean Patent Application No. 10-2014-0029765, filed on Mar. 13, 2014, in the Korean Intellectual Property Office, the disclosure of which is incorporated herein in its entirety by reference.

BACKGROUND

1. Field

One or more embodiments of the present invention relate to a medical diagnostic apparatus and a method of operating the medical diagnostic apparatus, and more particularly, to a medical diagnostic apparatus having functions of storing history of an operating state of the medical diagnostic apparatus that is modified according to a user input and returning to a predetermined operating state included in the history, and a method of operating the medical diagnostic apparatus.

2. Description of the Related Art

A medical diagnostic apparatus displays a medical image so as to provide a user with information about diagnosis of a disease and information for treatment. The medical diagnostic apparatus may be an additional apparatus separated from an apparatus for obtaining a medical image or may include an apparatus for obtaining a medical image. An apparatus for obtaining a medical image irradiates a predetermined signal toward an object and obtains a medical image about a cross-section or hematocele of the object by using a signal reflected from the object or a signal that has transmitted through the object.

For example, an apparatus for obtaining a medical image may obtain an ultrasound image, an X-ray image, a computerized tomography (CT) image, a magnetic resonance (MR) image, or a positron emission tomography (PET) image.

When a user controls a medical diagnostic apparatus such that the medical diagnostic apparatus performs operations that require precise user manipulation, to return to a previous operating state, the user has to input a command for restoring previously executed operations or execute each operation from an initial state. However, if the manipulation process is complicated, it is difficult for the user to remember all of inputs whereby all of corresponding operations are restored.

Also, if a precise manipulation is required, it is difficult in reality to operate a medical diagnostic apparatus such that the medical diagnostic apparatus returns to a previous operating state.

SUMMARY

One or more embodiments of the present invention include a medical diagnostic apparatus having functions of storing a history of an operating state of the medical diagnostic apparatus and returning to a previous state from among a plurality of operating states included in the history, and a method of operating the medical diagnostic apparatus.

Additional aspects will be set forth in part in the description which follows and, in part, will be apparent from the description, or may be learned by practice of the presented embodiments.

According to one or more embodiments of the present invention, a method of operating a medical diagnostic apparatus that displays a medical image, includes: modifying an operating state of the medical diagnostic apparatus from a first state to a second state based on sequential first user inputs; storing a history of a plurality of operating states respectively corresponding to the first user inputs; receiving a recovery input; selecting a third state from among the plurality of operating states included in the history, based on the recovery input; and modifying the operating state of the medical diagnostic apparatus from the second state to the third state.

The modifying the operating state of the medical diagnostic apparatus to the second state may include modifying a displaying method of displaying the medical image or modifying a parameter applied to the medical image.

The modifying of an operating state of the medical diagnostic apparatus to the second state may include modifying an ultrasound mode of a displayed medical image, modifying the number of medical images displayed on a single screen, and modifying a 2D medical image to a 3D medical image or from a 3D medical image to a 2D medical image.

The storing of a history may include: selecting at least one user input related to modification of an operating state of the medical diagnostic apparatus from among the first user inputs; and storing an operating state corresponding to the selected first user input as the history.

The selecting of the third state may include selecting an operating state just before the second state.

The selecting of the third state may include selecting the third state from among the plurality of operating states based on an input frequency or duration time of the recovery input.

The method may further include displaying the history, and the receiving of the recovery input may include receiving an input via which the third state from among the operating states is selected, with respect to the displayed history.

The storing of the history may include: determining the first state as an upper node and determining at least one operating state that is modified by the first user inputs as a subnode of the first state; and storing the history based on a tree structure formed of the upper node and the subnode.

The method may further include: receiving a second user input; modifying an operating state of the medical diagnostic apparatus from the third state to a fourth state based on the second user input; renewing the history such that the fourth state is further included as a subnode of the third state based on the tree structure and storing the history; and modifying an operating state of the medical diagnostic apparatus based on a recovery input, from the fourth state to the second state included in the history.

The modifying of an operating state of the medical diagnostic apparatus to the second state may include modifying a parameter applied to the medical image based on the first user inputs, from a first value to a second value, and the selecting of the third state may include selecting an operating state that returns from the second value to the first value by a predetermined value that is determined based on a user set up.

The storing of the history may include storing the history in a form that an external device uses to modify an operating state of the external device.

According to one or more embodiments of the present invention, a medical diagnostic apparatus includes: a display unit that displays a medical image based on an operating state of the medical diagnostic apparatus; a user input unit that receives sequential first user inputs and a recovery input; a storage unit that stores a history of a plurality of operating states respectively corresponding to the first user inputs; and a controller that modifies an operating state of the medical diagnostic apparatus from a first state to a second state based on the first user inputs, selects, based on the recovery input, a third state from among the plurality of operating states included in the history, and modifies the operating state of the medical diagnostic apparatus from the second state to the third state.

The controller may modify an operating state of the medical diagnostic apparatus to the second state by modifying a displaying method of displaying the medical image or by modifying a parameter applied to the medical image.

The controller may modify an operating state of the medical diagnostic apparatus to the second state by modifying an ultrasound mode of a displayed medical image, by modifying the number of medical images displayed on a single screen, or by modifying the medical image from a 2D mode to a 3D mode or from a 3D mode to a 2D mode.

The controller may select at least one of the first user inputs, which is related to modification of an operating state of the medical diagnostic apparatus, and the storage unit may store an operating state corresponding to the selected at least one first user input as the history.

The controller may select an operating state just before the second state as the third state.

The controller may select the third state from among the plurality of operating states based on an input frequency or a duration time of the recovery input.

The display unit may further display the history, and the user input unit may receive an input via which the third state is selected from among the operating states, with respect to the displayed history.

The controller may determine the first state as an upper node, and determine at least one operating state that is modified based on the first user inputs as a subnode of the first state, and the storage unit may store the history based on a tree structure formed of the upper node and the subnode.

The user input unit may further receive a second user input; the controller may modify an operating state of the medical diagnostic apparatus from the third state to a fourth state based on the second user input; the storage unit may renew the history such that the fourth state is further included as a subnode of the third state based on the tree structure and stores the history; and the controller may modify an operating state of the medical diagnostic apparatus based on a recovery input, from the fourth state to the second state included in the history.

The controller may modify an operating state of the medical diagnostic apparatus to the second state by modifying a parameter applied to the medical image based on the first user inputs, from a first value to a second value, and may select, as the third state, an operating state that returns from the second value to the first value by a predetermined value that is determined based on a user set up.

The storage unit may store the history in a form that an external device uses to modify an operating state of the external device.

According to one or more embodiments of the present invention, a non-transitory computer readable recording medium having embodied thereon a program for executing the method described above is included.

BRIEF DESCRIPTION OF THE DRAWINGS

These and/or other aspects will become apparent and more readily appreciated from the following description of the embodiments, taken in conjunction with the accompanying drawings in which:

FIGS. 8A, 8B, and 8C illustrates an example of a parameter input graphic user interface (GUI) displayed according to an embodiment of the present invention;

DETAILED DESCRIPTION

Figure 1:
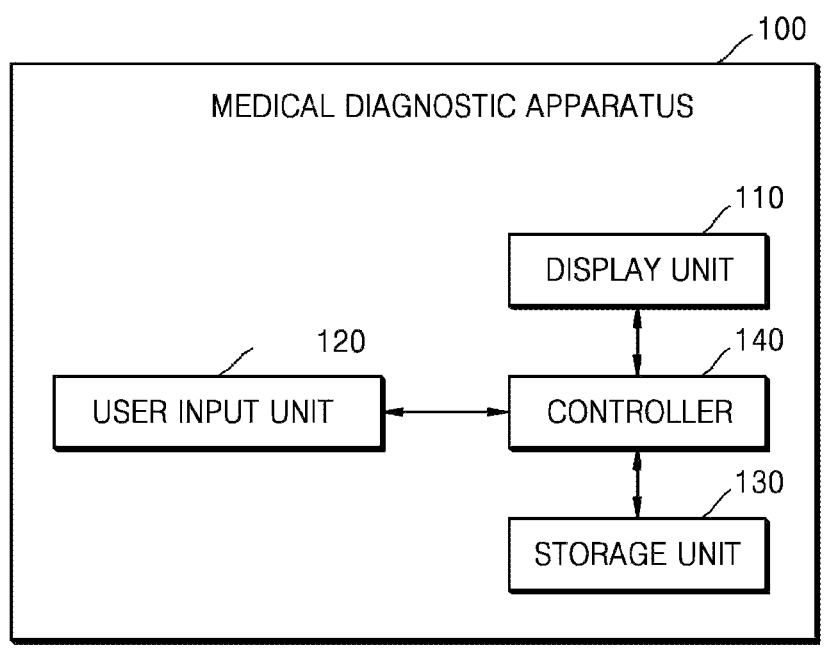
FIG. 1 is a block diagram illustrating a medical diagnostic apparatus according to an embodiment of the present invention.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Hereinafter, the present invention will be described in detail by explaining exemplary embodiments of the invention with reference to the attached drawings. The invention may, however, be embodied in many different forms, and should not be construed as being limited to the embodiments set forth herein; rather, these embodiments are provided so that this disclosure will be thorough and complete, and will fully convey the concept of the invention to those skilled in the art. In the following description, well-known functions or constructions are not described in detail since they would obscure the invention with unnecessary detail, and like reference numerals in the drawings denote like or similar elements throughout the specification.

Throughout the specification, it will also be understood that when an element is referred to as being "connected to" another element, it can be directly connected to the other element, or it can be electrically connected to the other element and intervening elements may be present. Also, when a part "includes" an element, unless there is a particular description contrary thereto, the part can further include other elements, not excluding the other elements.

Throughout the specification, a term 'object' may be an animated object or an inanimated object, which is displayed via an image. Also, the object may be a part of a human body and may include the liver, the heart, the womb, the brain, the breast, the abdominal region, or the like, a fetus, or a cross-section of a part of a human body. Throughout the specification, a "user" may be, without limitation, a medical expert including a doctor, a nurse, a medical laboratory technologist, a sonographer, a medical image expert, or the like.

A medical diagnostic apparatus provides a medical image about an object and is used in diagnosis and treatment of a disease. A medical diagnostic apparatus may obtain image data about an object, generate a medical image based on the image data, and display the medical image on a screen.

A user may operate a medical diagnostic apparatus such that the medical diagnostic apparatus transmits or receives a predetermined signal to or from an object in order to obtain image data, or sets various parameters needed to generate a medical image from image data, or modifies a displaying method of displaying the medical image on a screen. According to the conventional art, it is burdensome that after operating a medical diagnostic apparatus, a user has to operate a medical diagnostic apparatus from an initial state again in order to return to a previous state.

The present invention has been designed to solve the problem of the conventional art.

FIG. 1 is a block diagram illustrating a medical diagnostic apparatus 100 according to an embodiment of the present invention.

The medical diagnostic apparatus 100 according to the current embodiment of the present invention includes a display unit 110, a user input unit 120, a storage unit 130, and a controller 140.

The display unit 110 displays a medical image based on an operating state of the medical diagnostic apparatus 100. The display unit 110 may further display a history of the medical diagnostic apparatus 100 stored in the storage unit 130. The display unit 110 may display not only a medical image generated by using the medical diagnostic apparatus 100 but also various information processed in the medical diagnostic apparatus 100 through a graphic user interface (GUI).

The user input unit 120 receives a user input. A user input may refer to data or a signal that is input to the medical diagnostic apparatus 100 by a user. In detail, a user input may refer to data or a signal through which an event, which is a motive of initiating or completing a predetermined operation, is generated. A user input may be received through, for example, a control panel, a keyboard, and a touch panel included in the medical diagnostic apparatus 100.

For example, based on a first user input via which a medical image being displayed on a screen is rotated, moved, or expanded or reduced, the medical diagnostic apparatus 100 may output a new medical image that is obtained by rotating, moving or expanding or reducing a currently displayed medical image.

The user input unit 120 refers to a unit through which a user inputs data or a signal for operating the medical diagnostic apparatus 100. The user input unit 120 according to the current embodiment of the present invention sequentially receives a plurality of user inputs. The user input unit 120 may further include a recovery input via which an operating state of the medical diagnostic apparatus is modified to a predetermined operating state included in the history.

Examples of the user input unit 120 include, without limitation, a key pad, a dome switch, a mouse, a sensor, a knob button, a touch pad (capacitive overlay type, resistive overlay type, infrared beam type, integral strain gauge type, surface acoustic wave type, piezoelectric type or the like), a jog wheel, and a jog switch. Also, a touch pad which is in a layered structure with a display panel of the display unit 110 may be referred to as a touch screen.

In addition, the user input unit 120 may include a sensor that receives a temperature input, a pressure input, or a sound input or the like.

The storage unit 130 stores a history of a plurality of operating states of the medical diagnostic apparatus 100 respectively corresponding to user inputs. The storage unit 130 may store, from among a plurality of operating states, at least one operating state corresponding at least one user input selected by using the controller 140, as a history. Also, the storage unit 130 may store image data that is used to generate a medical image.

The controller 140 controls the overall operation of the medical diagnostic apparatus 100, and controls the display unit 110, the user input unit 120, and the storage unit 130 such that a medical image is displayed based on an operating state of the medical diagnostic apparatus 100. Also, the controller 140 may include a processor (not shown) that generates a medical image based on image data. Image data that the controller 140 uses to generate a medical image may be obtained from the storage unit 130 or may be generated by using the controller 140 based on a signal received from an object in response to a signal that is transmitted to the object, or may be received from an external device or an external server.

Also, the controller 140 modifies an operating state of the medical diagnostic apparatus 100 based on user inputs. For example, the controller 140 may modify an operating state of the medical diagnostic apparatus from a first state to a second state based on a plurality of first user inputs that are sequentially received.

The controller 140 may modify an operating state of the medical diagnostic apparatus by modifying a displaying method in which a medical image is displayed or by modifying a parameter applied to a medical image. The controller 140 may modify a displaying method, in which a medical image is displayed, by modifying the number of medical images displayed on a single screen or by modifying a 2D medical image to a 3D medical image or a 3D medical image to a 2D medical image.

Alternatively, when a displayed medical image is an ultrasound image, the controller 140 may modify a displaying method, in which a medical image is displayed, by modifying an ultrasound mode. Examples of an ultrasound mode include, without limitation, a brightness (B) mode in which an intensity of an echo signal reflected by an object is expressed by brightness, a Doppler (D) mode in which a Doppler component extracted from an echo signal is expressed by a color or a waveform, and an elastic mode in which a degree of deformation of a tissue according to a pressure applied from the outside is formed to an image.

The controller 140 may control an operation of the medical diagnostic apparatus 100 such that at least one of first user inputs that is related to modification of an operating state of the medical diagnostic apparatus 100 is selected and that the storage unit 130 stores an operating state corresponding to the selected, first user input as a history. A first user input related to modification of an operating state of the medical diagnostic apparatus 100 may refer to a first user input related to at least one selected from the group consisting of an operation of generating a medical image that is different from a medical image that the medical diagnostic apparatus 100 is currently displaying and an operation of displaying a medical image that is different from a medical image that the medical diagnostic apparatus 100 is currently displaying.

For example, the controller 140 may store, as a history of the medical diagnostic apparatus 100, only first user inputs except a first user input via which storage and output of a medical image or replay of medical video images is performed.

Next, the controller 140 may return to a previous operating state based on a recovery input. Based on the received recovery input, the controller 140 may select a predetermined state from among a plurality of states and return to the selected operating state. For example, the controller 140 may select a third state from among a plurality of operating states included in a history, and may modify an operating state of a medical diagnostic apparatus from the second state to the third state.

For example, the controller 140 may move to a predetermined state in a stepwise manner, from among a plurality of operating states included in a history, based on a recovery input.

For example, the controller 140 may modify a current operating state to a previous operating state just before the current operating state, from among a plurality of operating states included in a history, based on a recovery input. That is, when an operating state of the medical diagnostic apparatus 100 starts from "state A", passes "state B" and is modified to "state C", and a recovery input is received, the controller 140 may modify the operating state of the medical diagnostic apparatus 100 to "state B" which is an operating state just before "state C," which is a current operating state.

Alternatively, the controller 140 may modify an operating state of the medical diagnostic apparatus 100 to a selected state based on a recovery input via which a predetermined state is selected from among a plurality of operating states included in a history displayed by using the display unit 110.

For example, when an operating state of the medical diagnostic apparatus 100 starts from "state A", passes "state B" and is modified to "state C", the controller 140 may modify, based on a recovery input via which "state A" or "state B" is selected, the operating state of the medical diagnostic apparatus 100 to "state A" or "state B."

As described above, the medical diagnostic apparatus 100 according to the current embodiment of the present invention provides functions of storing a history of a plurality of operating state respectively corresponding to user inputs and returning to a predetermined operating state included in the history, thereby allowing a user to conveniently and easily operate the medical diagnostic apparatus 100.

Hereinafter, a method of operating the medical diagnostic apparatus 100 will be described in detail with reference to FIG. 2.

Figure 2:
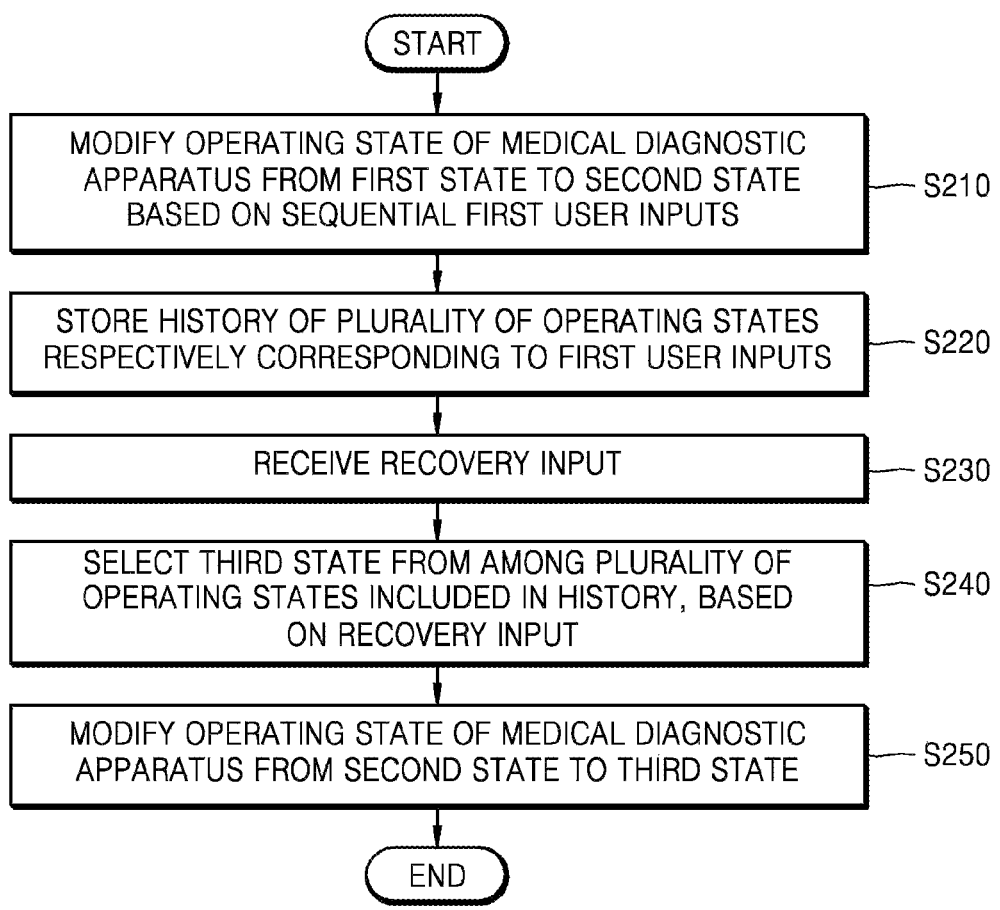
FIG. 2 is a flowchart illustrating a method of operating a medical diagnostic apparatus according to an embodiment of the present invention.

FIG. 2 is a flowchart illustrating a method of operating a medical diagnostic apparatus 100 according to an embodiment of the present invention.

In operation S210, the medical diagnostic apparatus 100 modifies an operating state of the medical diagnostic apparatus 100 from a first state to a second state based on sequential first user inputs.

A first user input may refer to a user input that is input by a user to the medical diagnostic apparatus 100. In detail, a user input may refer to data or a signal through which an event, which is a motive of initiating or completing a predetermined operation, is generated.

A first user input may be received via, for example, a control panel, a keyboard, and a touch panel included in the medical diagnostic apparatus 100. For example, based on a first user input via which a medical image being displayed on a screen is rotated, moved, or expanded or reduced, the medical diagnostic apparatus 100 may output a new medical image that is obtained by rotating, moving or expanding or reducing a currently displayed medical image.

The medical diagnostic apparatus 100 may obtain image data, generate a medical image based on the image data, and display the medical image on a screen.

Thus, modification of an operating state of the medical diagnostic apparatus 100 may refer to modification of a display method of displaying a medical image.

A method of displaying a medical image may be modified by modifying the number of medical images displayed on a single screen or by converting a 2D image to a 3D image or a 3D image to a 2D image. Alternatively, when the medical diagnostic apparatus 100 is an ultrasound diagnostic apparatus that provides an ultrasound image, a method of displaying a medical image may be modified as an ultrasound mode is modified.

Also, the medical diagnostic apparatus 100 may modify a parameter applied to a medical image from a first value to a second value, based on first user inputs.

Thus, modification of an operating state of the medical diagnostic apparatus 100 may refer to modification of a parameter that is applied to generate a medical image based on image data or modification of a parameter that is applied to display the generated medical image.

For example, the medical diagnostic apparatus 100 may display a 3D image displaying an object by rotating the 3D image by 90° with respect to a predetermined rotational axis based on a first user input via which a knob button on a control panel of the medical diagnostic apparatus 100 is rotated by a predetermined angle.

The medical diagnostic apparatus 100 may include, as a first user input, at least one selected from the group consisting of an input via which a gain applied to a medical image displayed on a screen such as a TGC (Time Gain Compensation) is modified, an input via which a dynamic range is modified, an input via which a post process is selected, an input via which geometry applied to a medical image is modified, and an input via which a depth applied to a medical image displayed on a screen is modified.

Also, the medical diagnostic apparatus 100 may modify an operating state thereof based on at least one selected from the group consisting of an input via which an irradiation angle of a predetermined signal irradiated to an object is adjusted, an input via which annotation, a marker, or a text is input with respect to an image displayed on a screen, and an input via which at least one selected from the group consisting of a length, a thickness, a size, and a shape of a predetermined area about an object is measured.

In operation S220, the medical diagnostic apparatus 100 according to the current embodiment of the present invention stores a history of a plurality of operating state respectively corresponding to first user inputs.

The medical diagnostic apparatus 100 may select at least one first user input related to an operating state of the medical diagnostic apparatus 100 from among first user inputs and store an operating state corresponding to the selected first user input as a history. The medical diagnostic apparatus 100 may obtain a medical image that is different from a currently displayed medical image, as a first user input related to modification of an operating state of the medical diagnostic apparatus 100, or may select only a first user input via which a medical image that is different from a currently displayed medical image is displayed on a screen.

The medical diagnostic apparatus 100 may store only an operating state corresponding to a first user input related to modification of an operating state of the medical diagnostic apparatus 100, as a history of the medical diagnostic apparatus 100, except a first user input related to at least one selected from the group consisting of an image output through a printer, storage of an image, storage of a video, replay or a video, and production of a video. Examples of a first user input related to modification of an operating state of the medical diagnostic apparatus 100 may include, without limitation, an input via which a parameter related to a focus of a predetermined signal transmitted to an object is set, an input via which a depth or an expansion rate of an image displayed on a screen is set, and an input via which an image displayed on a screen is rotated.

Also, the medical diagnostic apparatus 100 may store a history based on a tree structure. The medical diagnostic apparatus 100 may determine a first state as an upper node and at least one operating state that is modified via first user inputs as a subnode of the first state. The medical diagnostic apparatus 100 may store a history based on a tree structure formed of the determined upper node and the determined subnode.

A tree structure in which an operating state of the medical diagnostic apparatus 100 is stored according to an embodiment of the present invention will be described in detail with reference to FIGS. 9A, 9B, 9C, 10A, and 10B.

Meanwhile, the medical diagnostic apparatus 100 may store a history in a form that is available in an external device (for example, another medical diagnostic apparatus). An external device may modify an operating state to a predetermined operating state included in a history of the medical diagnostic apparatus 100 without receiving a new user input from a user by using a history stored in the medical diagnostic apparatus 100. Accordingly, when a complicated or precise operation is to be performed with respect to multiple medical diagnostic apparatuses, a user may achieve convenience by using the history stored in the medical diagnostic apparatus 100.

Also, according to an embodiment of the present invention, the medical diagnostic apparatus 100 may repeatedly perform arbitrary operations based on a history of a plurality of operating states. That is, the medical diagnostic apparatus 100 may select at least two of a plurality of operating states included in a history. Then, the medical diagnostic apparatus 100 may repeatedly perform operations within the history such that the medical diagnostic apparatus 100 is repeatedly modified from one operating state to another operating state.

In operation S230, the medical diagnostic apparatus 100 receives a recovery input.

A recovery input refers to a user input via which an operating state of the medical diagnostic apparatus 100 is returned to a desired operating state within a history. In detail, a recovery input may refer to data or a signal through which an event, through which an operating state of the medical diagnostic apparatus 100 is modified to a predetermined operating state of the past.

For example, a recovery input may be received through a GUI that supports a function of sequentially returning an operating state to a desired operating state within a history.

Figure 4A:
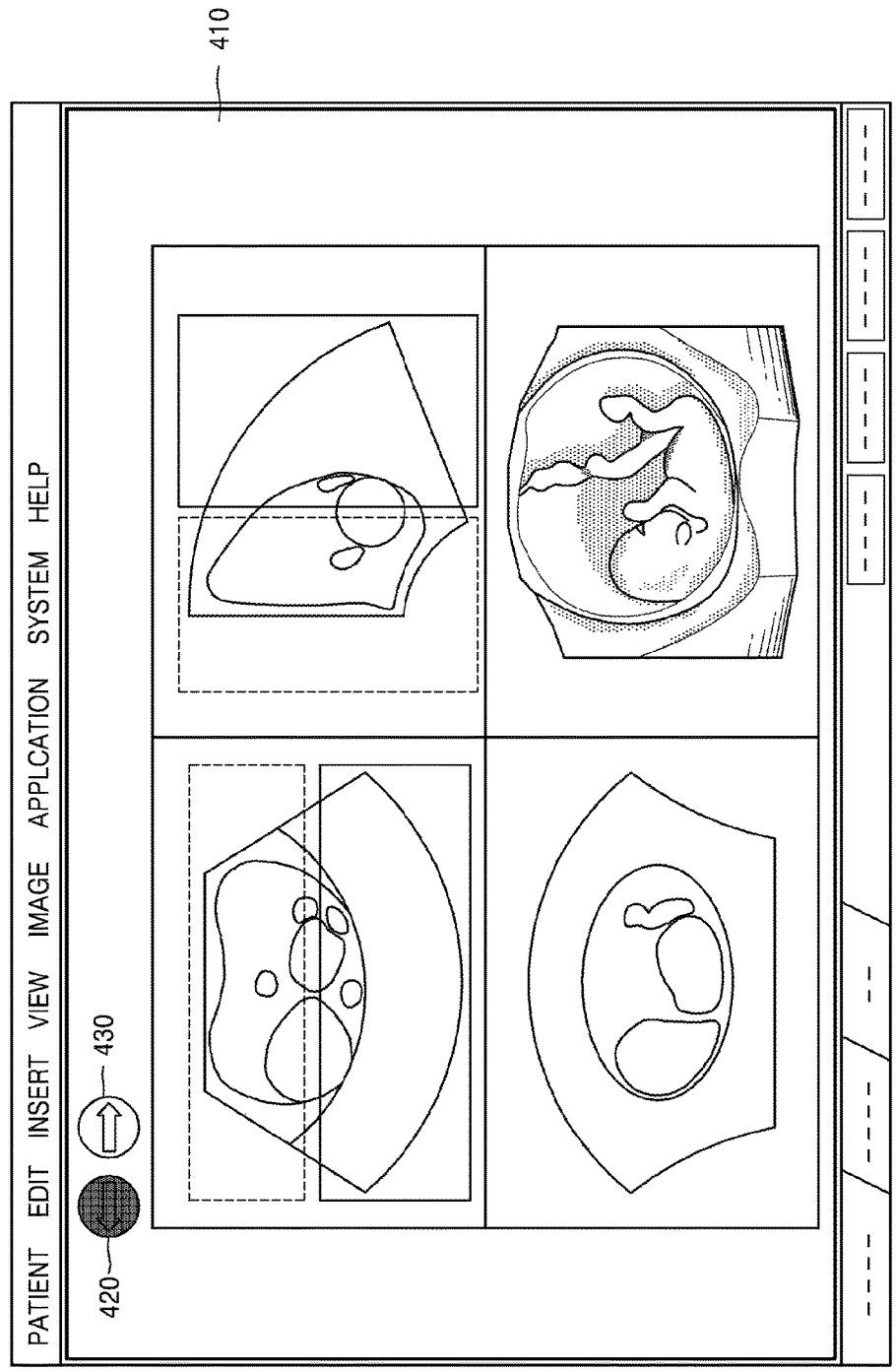
FIGS. 4A and 4B illustrate an example of a screen displayed according to an embodiment of the present invention.

FIG. 4A illustrates an example of a GUI 420 that supports a function of returning a current operating state to a previous state. The medical diagnostic apparatus 100 may modify an operating state of the medical diagnostic apparatus 100 to an operating state just before a current operating state from among a plurality of operating states included in a history, upon receiving a recovery input for selecting the GUI 420.

Alternatively, a recovery input may be received through icons that correspond to a plurality of operating states included in a history.

Figure 5A:
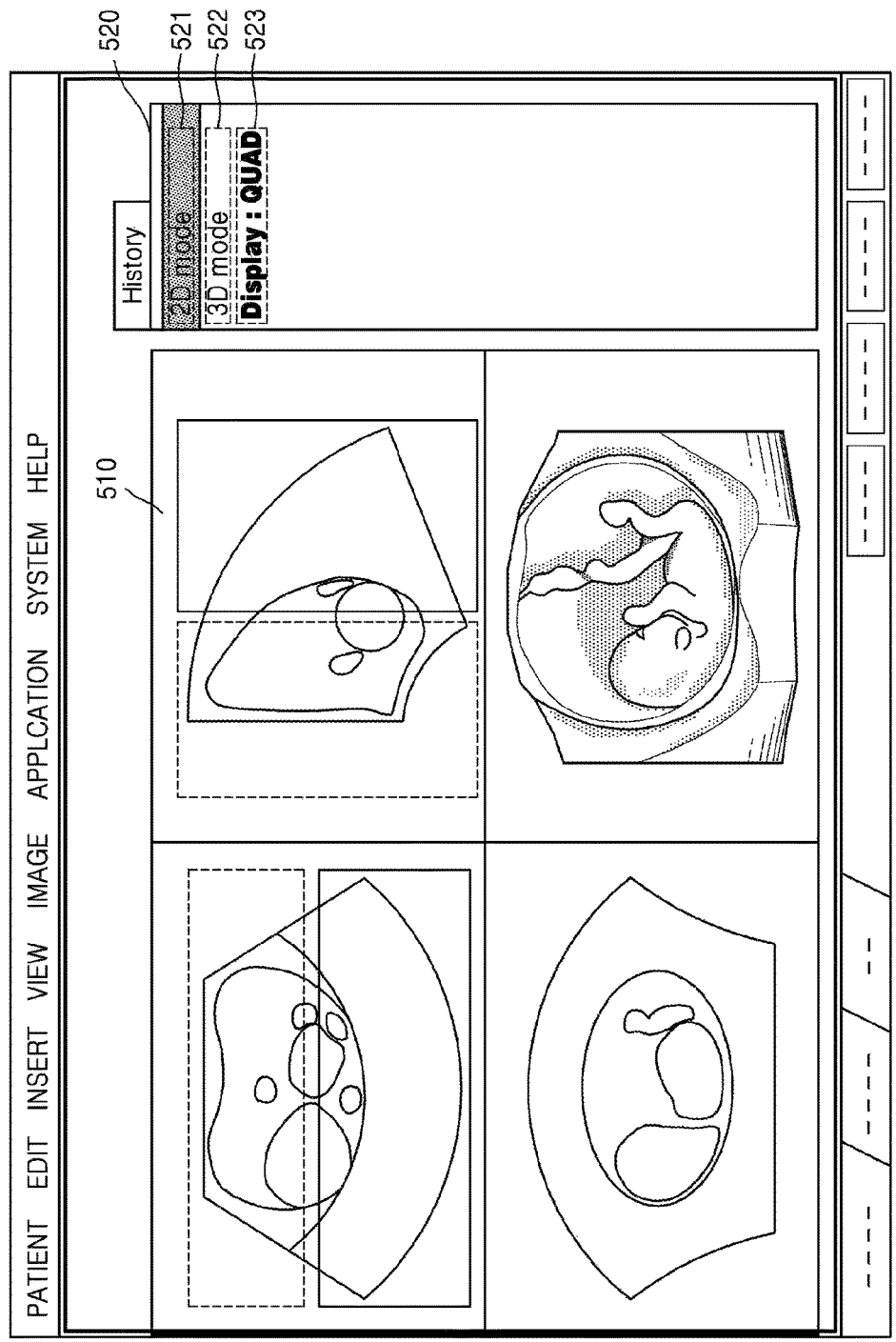
FIGS. 5A and 5B illustrate an example of a screen displayed according to another embodiment of the present invention.

As illustrated in FIG. 5A, the medical diagnostic apparatus 100 may display a history related to modification of an operating state of the medical diagnostic apparatus 100 on a predetermined area 520 of a screen. A history displayed on a screen may include icons 521, 522, and 523 corresponding to a plurality of operating states included in a history. Upon receiving a recovery input via which one of the icons 521, 522, and 523 corresponding to a plurality of operating states included in a history is selected, the medical diagnostic apparatus 100 may modify an operating state thereof to an operating state corresponding to the selected icon.

Meanwhile, the medical diagnostic apparatus 100 may align operating states included in a history of the medical diagnostic apparatus 100 displayed on a screen based on at least one selected from names, time, date, an ascending order, and a descending order.

In operation S240, the medical diagnostic apparatus 100 selects a third state from among the plurality of operating states included in a history, based on a recovery input.

The medical diagnostic apparatus 100 according to the current embodiment of the present invention may store a history based on a tree structure. The medical diagnostic apparatus 100 may determine a third state as an upper mode, and determine at least one operating state that is modified according to user inputs, as a subnode of a first node. Accordingly, the medical diagnostic apparatus 100 may determine the third state which is an operating state previous to the second state as an upper node of the second state, and store the second state and the third state within a history.

For example, the medical diagnostic apparatus 100 may select an operating state just before the second state as a third state, from among a plurality of operating states included in a history, based on a recovery input.

Alternatively, for example, the medical diagnostic apparatus 100 may select a third state corresponding to an input frequency or a duration time based on an input frequency or a duration time of a recovery input.

For example, when an input via which a GUI supporting a function of sequentially returning an operating state is selected n times is received, the medical diagnostic apparatus 100 may determine that a user input, which intends to return from a current operating state to an operating state before n operations, is received. Accordingly, an operating state of the medical diagnostic apparatus 100 may be modified from a current operating state to an operating state that is before n operations, based on an input frequency of a recovery input.

Alternatively, for example, the medical diagnostic apparatus 100 may receive, with respect to a history displayed on a screen, a third state from among operating states included in the history, and select a third state based on the received input.

In operation S250, the medical diagnostic apparatus 100 modifies the operating state thereof from the second state to the selected, third state.

The medical diagnostic apparatus 100 may modify an operating state thereof from an operating state that is just before the second state based on a recovery input, and may modify an operating state thereof to a state corresponding to an input frequency or a duration time of a recovery input.

Meanwhile, the operating state of the medical diagnostic apparatus 100 in operation S210 may be modified from a first state in which a predetermined parameter applied to a medical image is a first value to a second state in which a predetermined parameter is a second value based on first user inputs that are sequentially received. In this case, in operation S250, the medical diagnostic apparatus 100 may be modified from the second state to the third state based on a recovery input, and the third state may be an operating state in which the parameter returns from the second value to the first value by a predetermined value that is determined based on a user set up.

For example, an embodiment in which the medical diagnostic apparatus 100 is operated such that a 3D image displayed on a screen is rotated by 90° with respect to a predetermined axis by rotating a knob button on a control panel of the medical diagnostic apparatus 100 in a clockwise direction will be described as an example.

A state in which a 3D image is not rotated and thus a rotational angle is 0° may be regarded as a first state, and a state in which a rotational angle of a 3D image is 90° based on a first user input may be regarded as a second state. When a recovery input is received, the medical diagnostic apparatus 100 may operate such that the 3D image that is determined based on a user set up returns, by a predetermined angle, to a state before the 3D image is rotated. That is, the medical diagnostic apparatus 100 may determine θ° (θ>0) based on a user setup, and every time when a recovery input is received, the medical diagnostic apparatus 100 may display the 3D image that is rotated by 90° by each −θ°.

That is, according to an embodiment of the present invention, just by simply inputting a recovery input, the medical diagnostic apparatus 100 may be easily operated such that the medical diagnostic apparatus 100 returns to a predetermined operating state included in a history. Accordingly, according to the current embodiment of the present invention, the medical diagnostic apparatus 100 may search for operating states of the medical diagnostic apparatus 100 that are modified based on first user inputs or conveniently modify an operating state thereof to an arbitrary operating state from among a plurality of operating states included in a history. Accordingly, a user may save time needed to return to a previous operating state and achieve convenience.

Meanwhile, after modifying an operating state so as to return to a predetermined operating state included in a history based on a recovery input, the medical diagnostic apparatus 100 may receive a new user input and modify an operating state thereof based on the new user input.

For example, the medical diagnostic apparatus 100 may receive a second user input, and may modify an operating state of the medical diagnostic apparatus 100 from a third state to a fourth state based on the second user input.

A second user input may refer to a user input that is input to the medical diagnostic apparatus 100 by a user. In detail, a second user input may refer to data or a signal through which an event which is a motive for the medical diagnostic apparatus 100 to initiate or complete a predetermined operation is generated.

A second user input may be received through, for example, a control panel, a keyboard, and a touch panel included in the medical diagnostic apparatus 100. For example, based on a second user input via which a medical image being displayed on a screen is rotated, moved, or expanded or reduced, the medical diagnostic apparatus 100 may output, a new medical image that is obtained by rotating, moving or expanding or reducing a currently displayed medical image.

The first user input and the second user input may be user inputs that allow the medical diagnostic apparatus 100 to perform the same operation or different operations. Also, the first user input and the second user input may be received from the same user or from different users.

The medical diagnostic apparatus 100 that stores a history based on a tree structure may renew and store a history such that a fourth state is further included as a subnode of a third state. The medical diagnostic apparatus 100 that stores a history based on a tree structure stores an operating state history in parallel.

Accordingly, instead of storing the fourth state such that the fourth state which is newly added overwrites other operating states that are previously stored in a history, the medical diagnostic apparatus 100 may store the fourth state together in addition to other operating states that are previously stored. The medical diagnostic apparatus 100 that stores a history based on a tree structure may modify an operating state thereof from the fourth state to the second state included in the history based on a recovery input.

Figure 3:
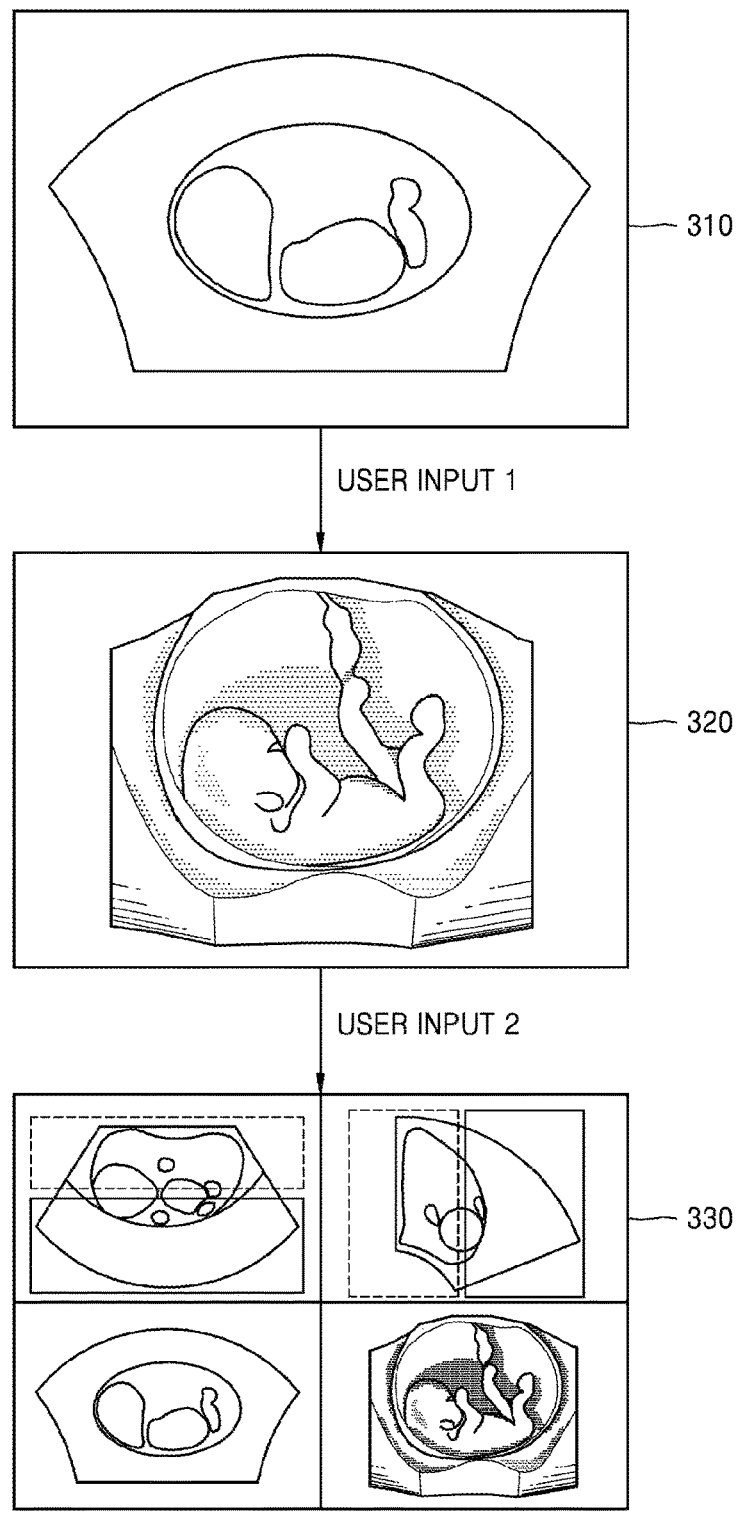
FIG. 3 is a schematic view to explain modification of an operating state of a medical diagnostic apparatus based on user inputs, according to an embodiment of the present invention.

Hereinafter, a method of operating the medical diagnostic apparatus 100 according to an embodiment of the present invention will be described in detail with reference to FIGS. 3, 4A, 4B, 5A, and 5B. FIG. 3 is a schematic view to explain modification of an operating state of a medical diagnostic apparatus based on user inputs, according to an embodiment of the present invention.

As illustrated in FIG. 3, the medical diagnostic apparatus 100 may display, on a screen, a 2D ultrasound image 310 of an embryo, a 3D ultrasound image 320 corresponding to the 2D ultrasound image 310 of the embryo based on a "user input 1", and a 4-segmented image 330 corresponding to the 3D ultrasound image 320 of the embryo based on a "user input 2". The medical diagnostic apparatus 100 may store a history of a plurality of operating states corresponding to "user input 1" and "user input 2." FIGS. 4A, 4B, 5A, and 5B illustrate a method of operating the medical diagnostic apparatus 100 based on a history of a plurality of operating states illustrated in FIG. 3.

Figure 4B:
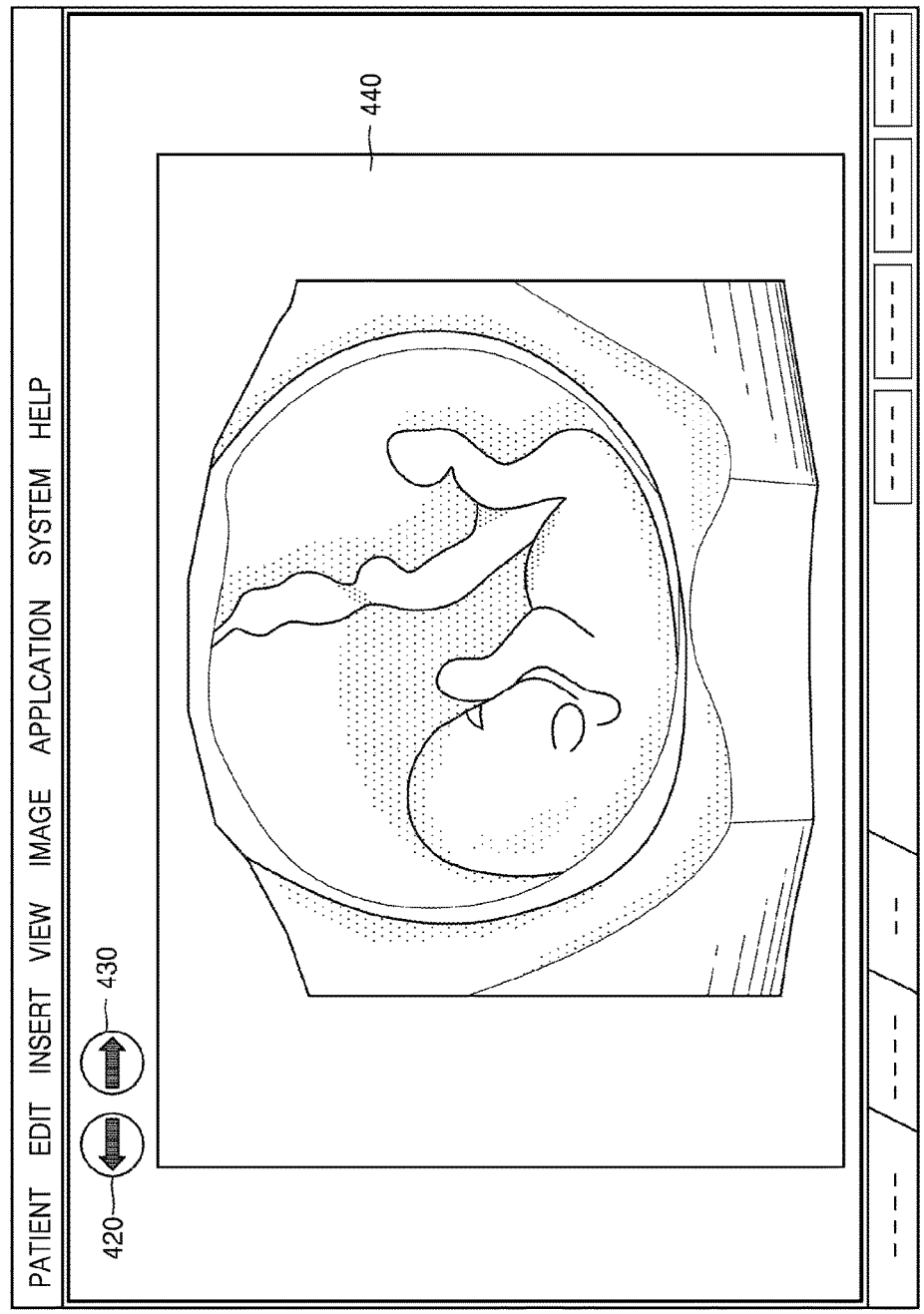

FIGS. 4A and 4B illustrate an example of a screen provided by the medical diagnostic apparatus 100 that provides a function of sequentially returning an operating state, according to an embodiment of the present invention.

The medical diagnostic apparatus 100 may provide a GUI 420 supporting a function of moving to a state previous to a current operating state and a GUI 430 supporting a function of moving to a next state to the current operating state.

As illustrated in FIG. 4A, the medical diagnostic apparatus 100 provides a 4-segmented image 410 about an embryo by using a medical image display method. The medical diagnostic apparatus 100 may receive a recovery input via which the GUI 420 is selected and modify an operating state thereof just before an operating state, to a current operating state. As illustrated in FIG. 4B, the medical diagnostic apparatus 100 returns to an operating state just before a current operating state (that is, a state before an operation corresponding to "user input 2" which is a recent user input in the history is performed) based on an input via which the GUI 420 is selected in FIG. 4A, thereby providing an 3D ultrasound image 440 of the embryo.

Figure 5B:
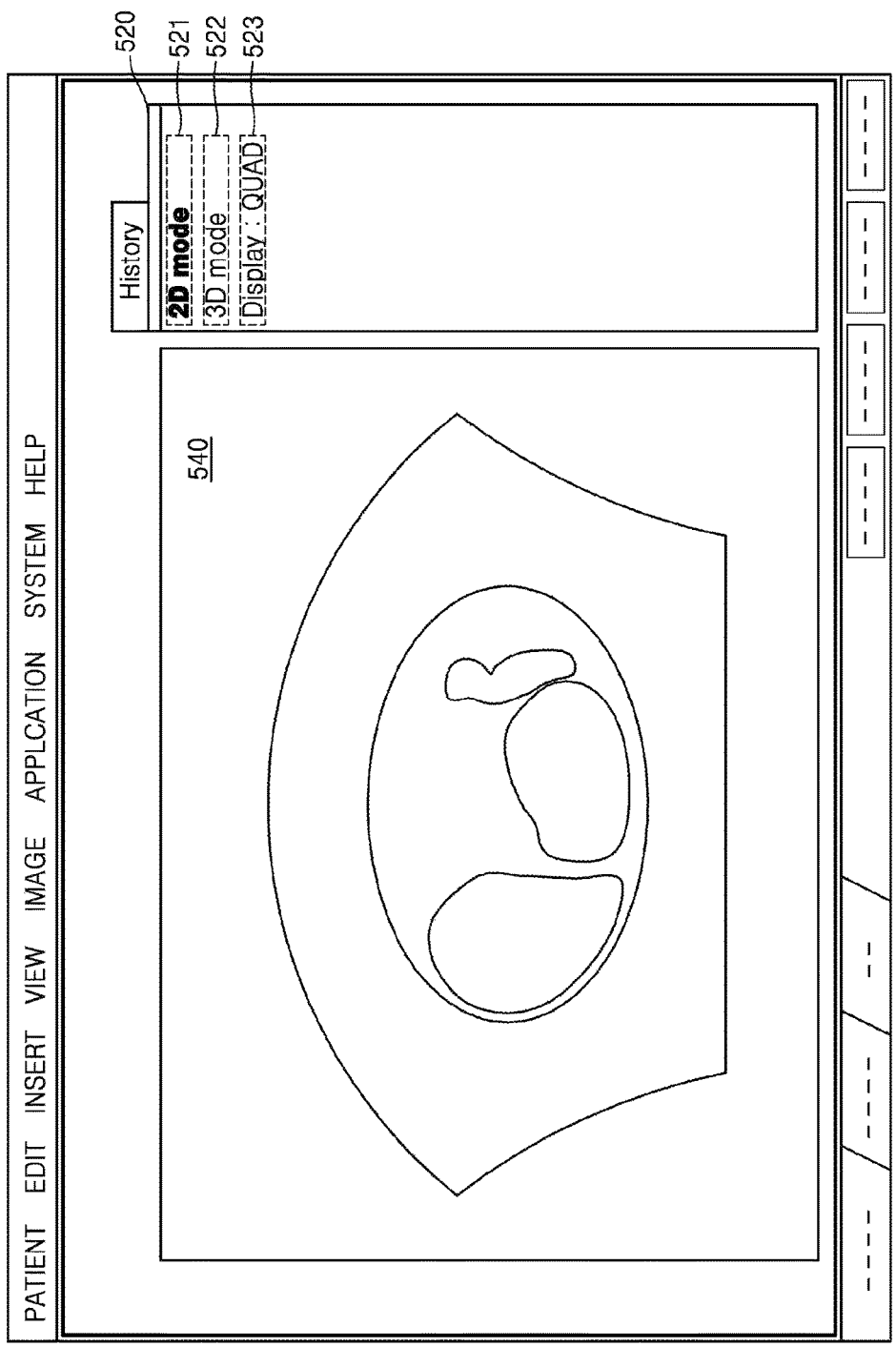

FIGS. 5A and 5B illustrate an example of a screen provided by using the medical diagnostic apparatus 100 that provides functions of displaying a history of modification of an operating state of the medical diagnostic apparatus 100 on a screen and returning to a predetermined operating state on a history based on a recovery input about the displayed history, according to an embodiment of the present invention.

As illustrated in FIG. 5A, the medical diagnostic apparatus 100 may display a history of modification of an operating state of the medical diagnostic apparatus 100 on a predetermined area 520 of a screen. A history displayed on the screen may include icons 521, 522, and 523 corresponding to a plurality of operating states included in the history. Upon receiving a recovery input via which one of the icons 521, 522, and 523 is selected, the medical diagnostic apparatus 100 may modify a current operating state thereof to an operating state corresponding to the selected icon.

As illustrated in FIG. 5A, the medical diagnostic apparatus 100 provides a 4-segmented image 510 of an embryo by using a medical image displaying method. Solid letters within the icon 523 indicate that an operating state corresponding to the icon 523 is a current operating state.

The medical diagnostic apparatus 100 may modify an operating state thereof to an operating state corresponding to the icon 521 by receiving a recovery input via which the icon 521 from among the icons 521, 522, and 523 corresponding to a plurality of operating states is selected.

When an input via which the icon 521 is selected is received in FIG. 5A, the medical diagnostic apparatus 100 returns to an operating state corresponding to the icon 521 (that is, an operating state before operations corresponding to "user input 1" and "user input 2" are performed) as illustrated in FIG. 5B, thereby providing a 2D ultrasound image 540 of the embryo. Solid letters within the icon 521 in FIG. 5B indicate that an operating state corresponding to the icon 521 is a current operating state.

As described above with reference to FIGS. 3, 4A, 4B, 5A, and 5B, the medical diagnostic apparatus 100 according to the current embodiment of the present invention may modify an operating state thereof by modifying a displaying method of displaying a medical image. However, the embodiments of the present invention are not limited thereto, and the medical diagnostic apparatus 100 may also modify an operating state thereof by modifying a parameter applied to a medical image.

Hereinafter, a method of operating the medical diagnostic apparatus 100 according to the current embodiment of the present invention will be described in detail with reference to FIGS. 6A, 6B, 6C, 7, 8A, 8B, and 8C.

Figure 6A:
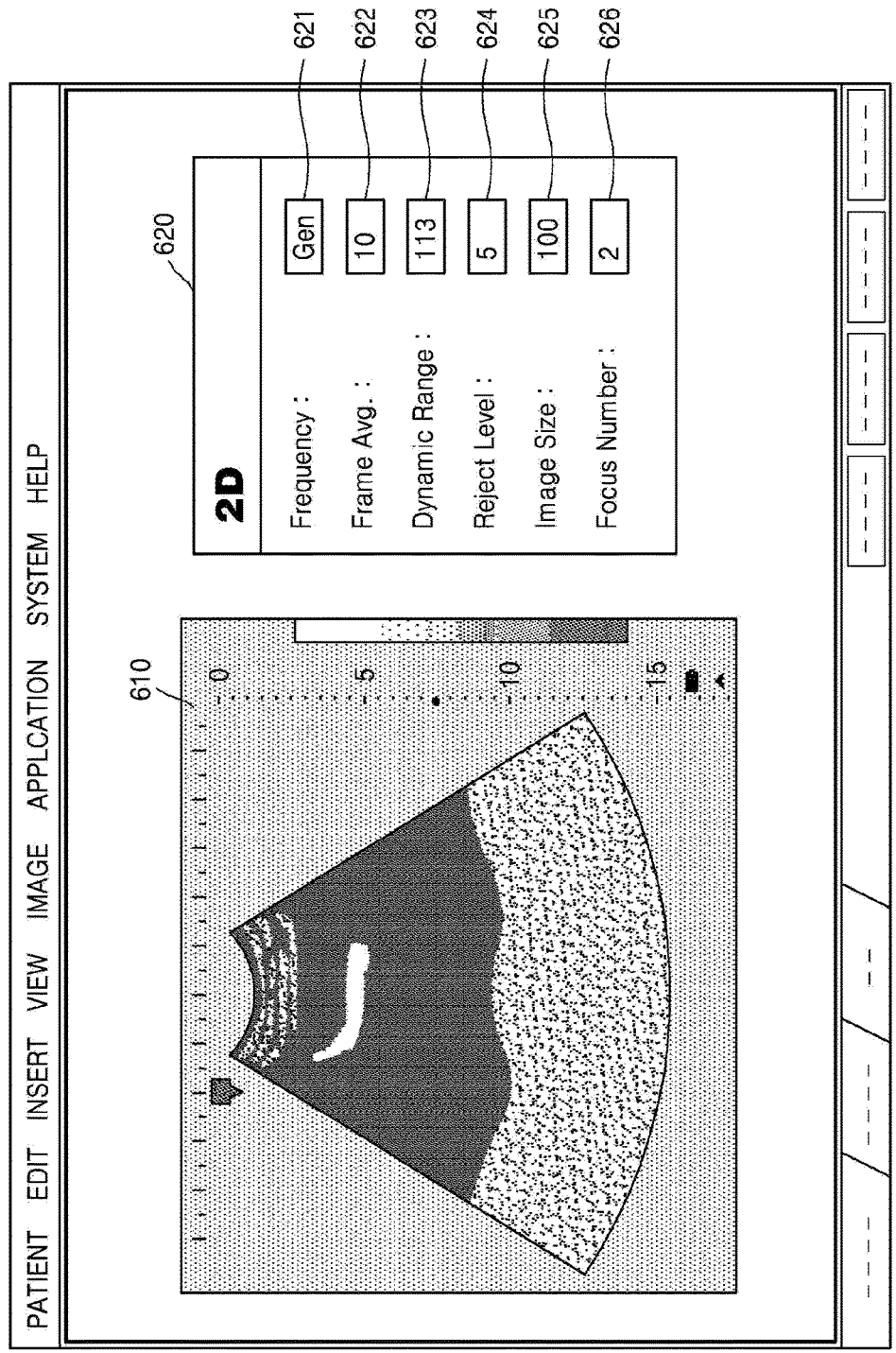
FIGS. 6A, 6B, and 6C illustrate an example of a screen displayed according to another embodiment of the present invention.
Figure 6B:
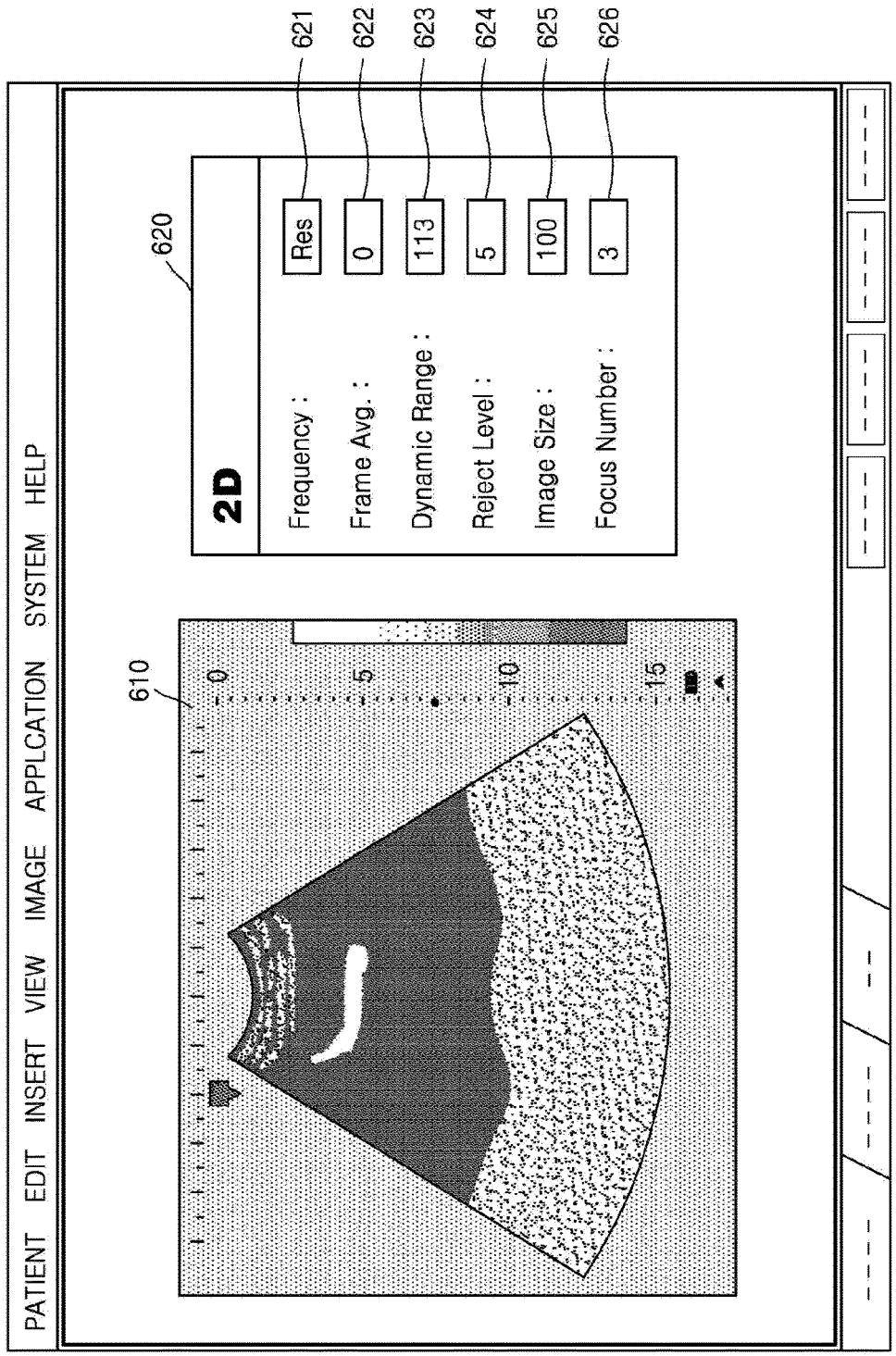
Figure 6C:
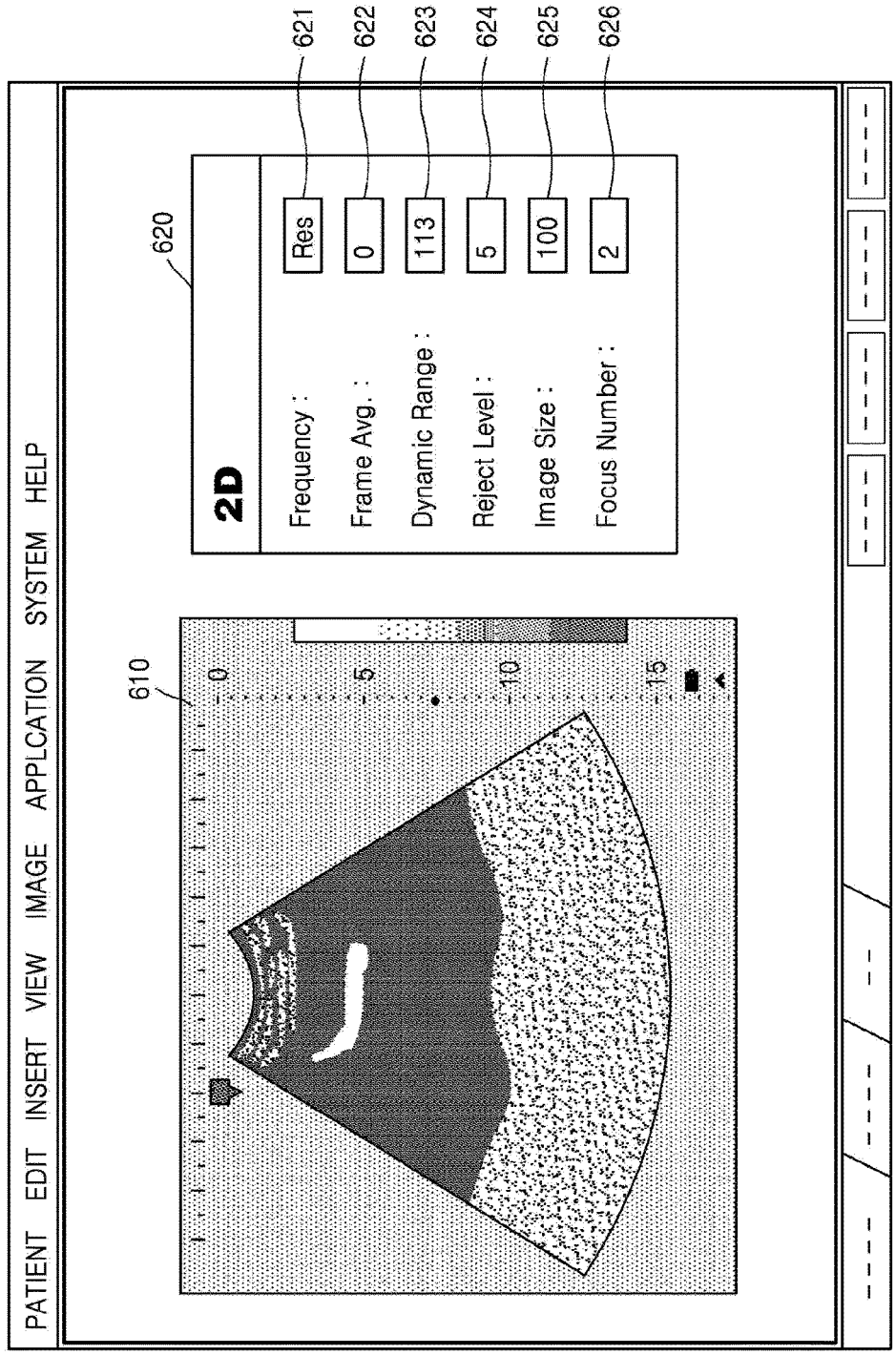

FIGS. 6A, 6B, and 6C illustrate an example of a screen displayed according to another embodiment of the present invention, in which an operating state that is modified based on user inputs to modify parameters is stored as a history.

As illustrated in FIGS. 6A, 6B, and 6C, the medical diagnostic apparatus 100 may display a GUI 620 through which a parameter applied to the medical image 610 is input by a user.

While a medical image displayed on the screen of FIGS. 6A, 6B, and 6C is an ultrasound 2D B mode image, the embodiments of the present invention are not limited thereto.

As illustrated in FIGS. 6A, 6B, and 6C, the GUI 620, through which a parameter applied to the medical image 610 is to be input, may include a UI 621 through which a frequency of an ultrasound signal transmitted from a probe in order to obtain the medical image 610 is received, a UI 622 through which a parameter value applied to average a current image and an image just before the current image is received, a UI 623 through which a ratio between a minimum value and a maximum value of an image data signal is received in order to adjust a contrast of the medical image 610, a UI 624 through which a degree of eliminating noise or echo is received in order to make the medical image 610 clear, a UI 625 through which a set up value for setting up a size of the medical image 610 is received, and a UI 626 through which a set up value for setting the number of focusing points for obtaining the medical image 610 is received. However, the embodiments of the present invention are not limited thereto, and it is obvious to one of ordinary skill in the art that the medical diagnostic apparatus 100 according to the current embodiment of the present invention may receive various parameters applied to a medical image by a user.

The medical diagnostic apparatus 100 may modify an operating state of the medical diagnostic apparatus 100 from the first state illustrated in FIG. 6A to the second state illustrated in FIG. 6B by modifying a parameter applied to a medical image.

FIG. 6A illustrates an example in which a Gen (General) mode in which a general frequency is set as a frequency value of a transmission ultrasound signal is selected on the UI 621. FIG. 6B illustrates an example in which a Res (Resolution) mode in which a relatively high frequency is set as a frequency value of a transmission ultrasound signal is selected on the UI 621. As illustrated in FIG. 6B, the medical diagnostic apparatus 100 may modify an operating state thereof by receiving a user input through which a frequency value of a transmission ultrasound signal is modified from a general frequency to a relatively high frequency.

FIG. 6A illustrates that "10" is input to the UI 622 as a parameter value applied to average a current image and an image just before the current image. FIG. 6B illustrates that "0" is input to the UI 622 as a parameter applied to image averaging. As illustrated in FIG. 6B, the medical diagnostic apparatus 100 may modify an operating state thereof by receiving a user input through which the parameter value applied to the image averaging is modified from "10" to "0."

Also, FIG. 6A illustrates that "2" is input to the UI 626 as a set up value for setting the number of foci for obtaining the medical image 610. FIG. 6B illustrates that "3" is input to the UI 626 as a set up value of the foci. As illustrated in FIG. 6B, the medical diagnostic apparatus 100 may modify an operating state thereof by receiving a user input through which a set up value of the foci is modified from "2" to "3."

Meanwhile, the medical diagnostic apparatus 100 displaying FIG. 6B may receive a recovery input from the user to display a screen as illustrated in FIG. 6C.

The medical diagnostic apparatus 100 may return to a predetermined state from among a plurality of operating states included in a history based on a recovery input of a user. For example, the medical diagnostic apparatus 100 may operate an operating state thereof from an operating state just before a current operating state. Accordingly, the medical diagnostic apparatus 100 may return to an operating state before a user input through which a set up value of the number of foci is modified from "2" to "3" is received, which is an operating state just before a current operating state corresponding to FIG. 6B. That is, as illustrated in FIG. 6C, the medical diagnostic apparatus 100 may return the set up value of the number of foci which is modified to "3" to "2" based on the recovery input.

Accordingly, a user may easily control the medical diagnostic apparatus 100 according to the current embodiment of the present invention such that the medical diagnostic apparatus 100 returns to a previous operating state, just by inputting a recovery input.

Figure 7:
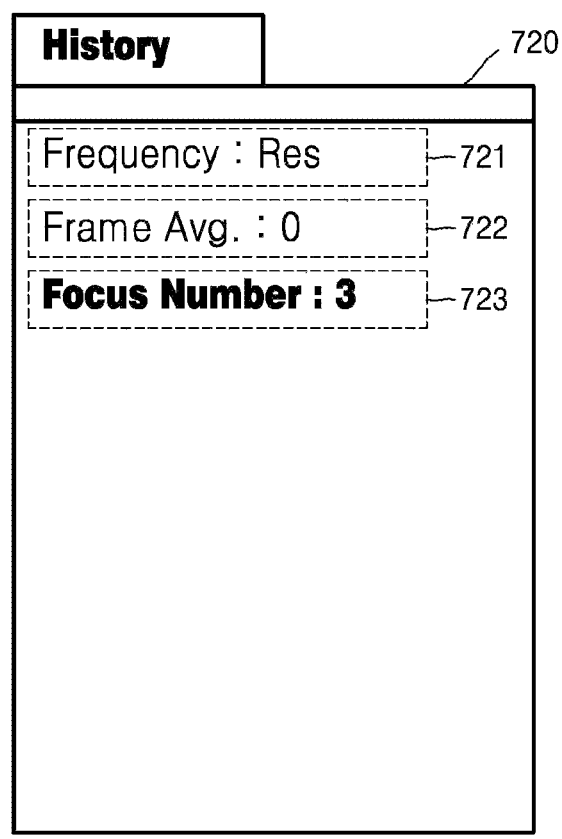
FIG. 7 illustrates an example of a screen on which an operating state history of a medical diagnostic apparatus that is stored is displayed, according to an embodiment of the present invention.

Meanwhile, as illustrated in FIG. 7, the medical diagnostic apparatus 100 may display a history 720 of an operating state that is stored. The medical diagnostic apparatus 100 may display a history related to modification of an operating state of the medical diagnostic apparatus 100 on a predetermined area of the screen.

The history 720 displayed on the screen may include icons 721, 722, and 723 respectively corresponding to a plurality of operating states that are modified based on user inputs. FIG. 7 In FIG. 7, a history 720 showing an operating state of the medical diagnostic apparatus 100 from the operating state illustrated in FIG. 6A to the operating state illustrated in FIG. 6B is illustrated. As illustrated in FIG. 7, the medical diagnostic apparatus 100 may store parameter values that are input by a user in order to modify an operating state thereof, and may output the parameter values on the screen.

The medical diagnostic apparatus 100 may receive a recovery input via which one of the icons 721, 722, and 723 corresponding to a plurality of operating states included in the history 720 to thereby modify an operating state thereof corresponding to the selected icon.

As illustrated in FIG. 7, solid letters within the icon 723 indicate that an operating state corresponding to the icon 523 is a current operating state. That is, the history 720 illustrated in FIG. 7 corresponds to the operating state of the medical diagnostic apparatus 100 illustrated in FIG. 6B.

The medical diagnostic apparatus 100 may receive a recovery input via which the icon 722 from among the icons 721, 722, and 723 corresponding to a plurality of operating states is selected, to thereby modify an operating state thereof corresponding to the icon 722. When an input via which the icon 722 is selected is received during the operating state illustrated in FIG. 6B, the medical diagnostic apparatus 100 may return to an operating state corresponding to the icon 722 as illustrated in FIG. 6C (that is, an operating before a user input via which a set up value of the number of foci is modified from "2" to "3" is received), thereby returning the set up value of the number of foci to a set up value of the past.

Meanwhile, a GUI through which a parameter applied to the medical image 610 is applied from a user may be provided in various forms. FIGS. 8A, 8B, and 8C illustrate an example of a screen provided by the medical diagnostic apparatus 100 according to an embodiment of the present invention, in which an operating state of the medical diagnostic apparatus that is modified based on user inputs for modifying a parameter is stored as a history.

As illustrated in FIGS. 8A, 8B, and 8C, the medical diagnostic apparatus 100 according to the current embodiment of the present invention may display a GUI 820 via which a parameter applied to a medical image is received from a user, on a screen.

FIGS. 8A, 8B, and 8C illustrate an example where a medical image displayed on a screen is an ultrasound color Doppler mode, but the embodiments of the present invention are not limited thereto.

As illustrated in FIGS. 8A, 8B, and 8C, the GUI 820, through which a parameter applied to the medical image 810 is to be input, may include a UI 821 through which a frequency of an ultrasound signal transmitted from a probe in order to obtain a medical image is received, a UI 822 through which a set up value for adjusting a transmission angle of an ultrasound transmitted from a probe is received, a UI 823 through which a blending level applied when overlapping a color Doppler image and a B mode image and providing the overlapped image is received, a UI 824 through which a blocking frequency value in regard to high band pass filtering of ultrasound image received at the probe is received, and a UI 825 through which a brightness limit value of a B mode area that is provided while being overlapped with a color Doppler image in order to adjust a range where the color Doppler image is displayed, is received. However, the embodiments of the present invention are not limited thereto, and it is obvious to one of ordinary skill in the art that the medical diagnostic apparatus 100 according to the current embodiment of the present invention may receive various parameters applied to a medical image, from a user.

The medical diagnostic apparatus 100 may modify an operating state thereof from the first state illustrated in FIG. 8A to the second state illustrated in FIG. 8B by modifying a parameter applied to a medical image.

That is, FIG. 8A illustrates an example where a "None" mode is selected, in which a transmission angle of an ultrasound signal is adjusted such that an area of interest is set as a front surface, on the UI 822. FIG. 8B illustrates an example where a "Right" mode is selected, in which a transmission angle of an ultrasound is adjusted such that an area of interest is set as a right side, on the UI 822. As illustrated in FIG. 8B, the medical diagnostic apparatus 100 may modify an operating state thereof by receiving a user input via which an area of interest is modified from a front surface to a right side, by adjusting a transmission angle of an ultrasound signal.

FIG. 8A illustrates an example where "24%" is input to the UI 823 as a mixture ratio of a color Doppler image and a B mode image. FIG. 8A illustrates an example where "0%" is input to the UI 823 as a mixture ratio of a color Doppler image and a B mode image. As illustrated in FIG. 8B, the medical diagnostic apparatus 100 may modify an operating state thereof by receiving a user input via which a mixture ratio of a color Doppler image and a B mode image is modified from "24%" to "0%."

Also, FIG. 8A illustrates an example where "24" is input to the UI 825 as a brightness limit of a B mode area which is provided while being overlapped with a color Doppler image. FIG. 8B illustrates an example where "15" is input to the UI 825 as a brightness limit of a B mode area which is provided while being overlapped with a color Doppler image. As illustrated in FIG. 8B, the medical diagnostic apparatus 100 may modify an operating state thereof by receiving a user input via which a brightness limit is modified from "24" to "15."

Meanwhile, the medical diagnostic apparatus 100 that displays FIG. 8B may receive a recovery input from a user to display a screen as illustrated in FIG. 8C. The medical diagnostic apparatus 100 may return to a predetermined state from among a plurality of operating states included in a history based on the recovery input of the user.

For example, the medical diagnostic apparatus 100 may modify an operating state thereof such that a parameter value is recovered by a predetermined value that is determined based on a user set up. FIG. 8C illustrates an example where a parameter value is returned by "3" with respect to a brightness limit value based on a recovery input. As illustrated in FIGS. 8A, 8B, and 8C, the medical diagnostic apparatus 100 may modify a brightness limit from "24" to "15" based on a user input, and may return from "15" to "24" by "3" based on the recovery input.

Accordingly, a user may easily control the medical diagnostic apparatus 100 according to the current embodiment of the present invention such that the medical diagnostic apparatus 100 returns to a previous operating state, just by inputting a recovery input.

FIGS. 9A, 9B, 9C, 10A, and 10B are views to explain that an operating state of the medical diagnostic apparatus 100 is stored based on a tree structure, according to embodiments of the present invention.

Figure 9A:
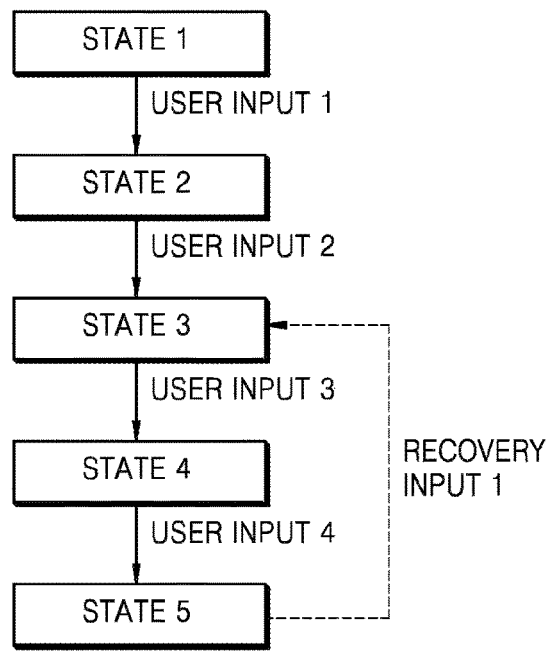
FIGS. 9A, 9B, 9C, 10A, and 10B are views to explain that an operating state of a medical diagnostic apparatus is stored based on a tree structure, according to embodiments of the present invention.

As illustrated in FIG. 9A, the medical diagnostic apparatus 100 may modify "state 1" to "state 5" based on a plurality of user inputs (that is, user inputs 1 through 4). The medical diagnostic apparatus 100 may store a plurality of operating states respectively corresponding to user inputs (that is, states 1 through 5) as a history of the medical diagnostic apparatus 100.

According to the current embodiment of the present invention, the medical diagnostic apparatus 100 may select "state 3" from among a plurality of operating states included in a history based on "recovery input 1" and modify an operating state thereof from "state 5" to "state 3" as illustrated in FIG. 6.

After modifying an operating state of the medical diagnostic apparatus 100 from "state 5" to "state 3" based on "recovery input 1," the medical diagnostic apparatus 100 may modify an operating state thereof based on an additionally input user input. Also, an operating state of the medical diagnostic apparatus 100 that is modified based on a user input that is additionally received may also be stored as a history of the medical diagnostic apparatus 100.

Here, a medical diagnostic apparatus which stores a history according to the conventional, sequential storage method stores "state 6" and "state 7" instead of "state 4" and "state 5" which are stored as operating states after "state 3" when storing a history of operating states respectively corresponding to "user input 5" and "user input 6." That is, as operating states after "state 3", "state 6" and "state 7" are stored, and the previously stored "state 4" and "state 5" are removed. Thus, the medical diagnostic apparatus which stores a history according to the conventional, sequential storage method is not able to return from "state 7" to "state 4" or "state 5" based on a recovery input.

However, according to the current embodiment of the present invention, a history of modification of an operating state of the medical diagnostic apparatus 100 may be stored based on a tree structure. FIG. 9C is a diagram to explain storage of a history of modification of an operating state of the medical diagnostic apparatus 100 according to an embodiment of the present invention, based on a tree structure.

A tree structure refers to a type of data structure in which nodes that designate information are branched off like branches with respect to an uppermost root node as a vertex. The medical diagnostic apparatus 100 that stores a history based on a tree structure determines a first state as an upper mode, and determines at least one operating state that is modified by sequential first user inputs, as a subnode of the first state. The medical diagnostic apparatus 100 stores a history based on a tree structure that is formed of the upper mode and the subnode.

As illustrated in FIG. 9A, the medical diagnostic apparatus 100 may modify an operating state thereof from "state 5" to "state 3." After modifying the operating state from "state 5" to "state 3," the medical diagnostic apparatus 100 may receive "user input 5" and "user input 6" as illustrated in FIG. 8.

The medical diagnostic apparatus 100 may modify an operating state thereof from "state 3" to "state 7" based on "user input 5" and "user input 6." The medical diagnostic apparatus 100 may store a history of operating states that respectively correspond to "user input 5" and "user input 6" (that is, state 6 and state 7).

Figure 9B:
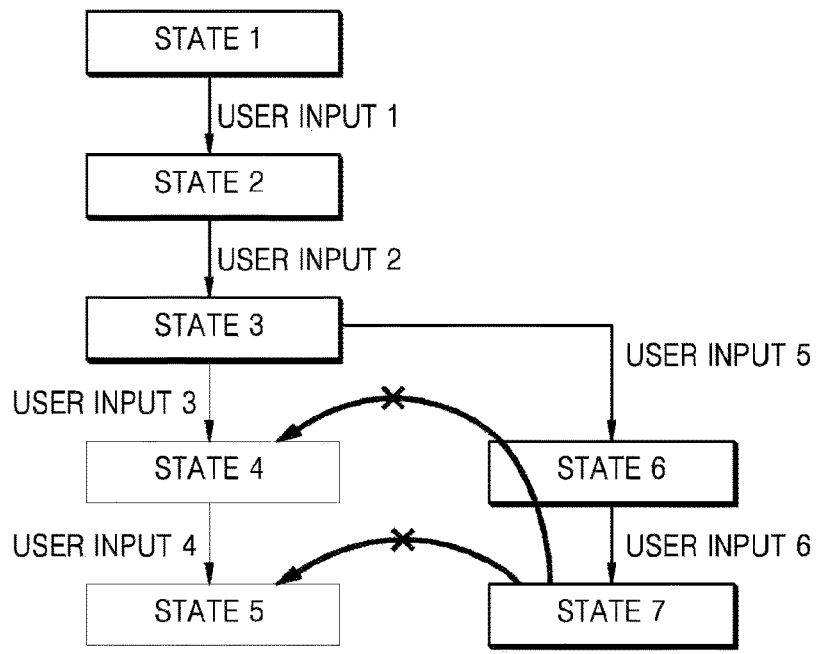
Figure 9C:
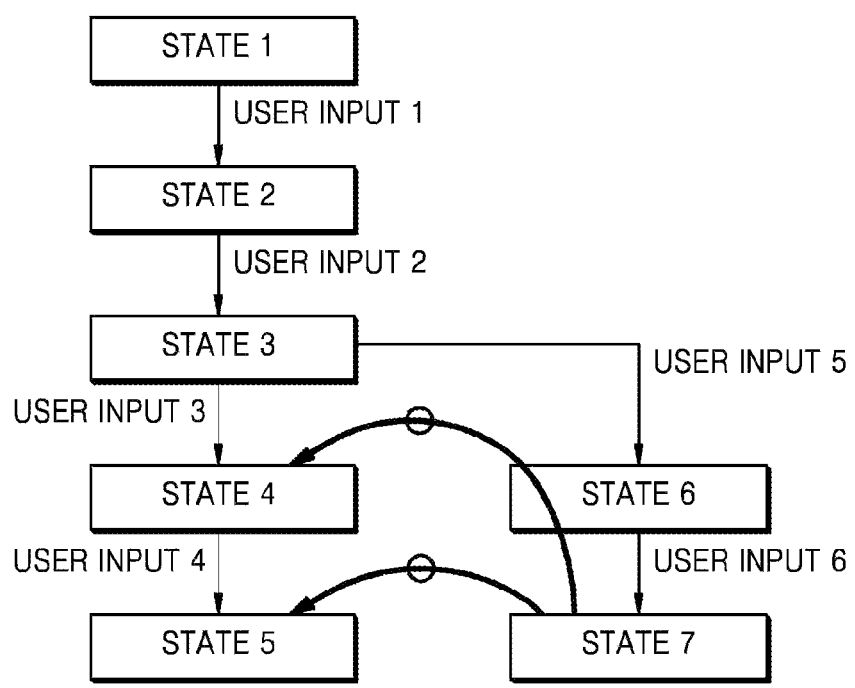

Here, when storing a history of operating states respectively corresponding to "user input 5" and "user input 6," the medical diagnostic apparatus 100 may renew a history such that "state 6" and "state 7" are included as subnodes of "state 3" in addition to "state 4" and "state 5." That is, unlike the sequential storage method illustrated in FIG. 9B, according to a storage method based on a tree structure, when storing "state 6" and "state 7," "state 4" and "state 5" are not removed.

In addition, as illustrated in FIG. 9C, the medical diagnostic apparatus 100 may modify an operating state thereof "state 7" to "state 4" or "state 5" based on a received recovery input. Thus, according to the medical diagnostic apparatus 100 of the current embodiment of the present invention, by storing a history according to a tree structure, the medical diagnostic apparatus 100 may return to any operating state of the past.

Figure 10A:
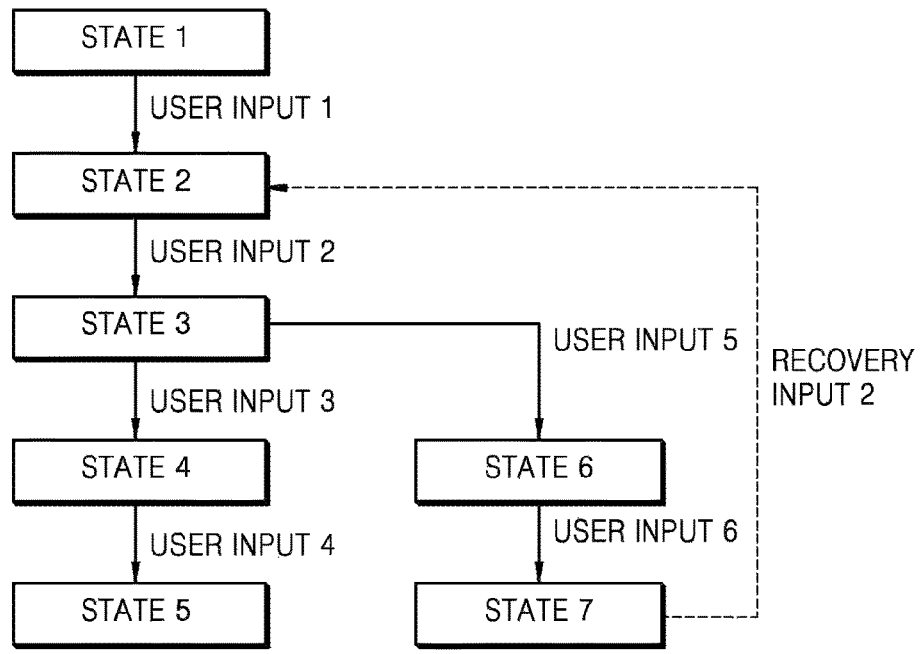
Figure 10B:
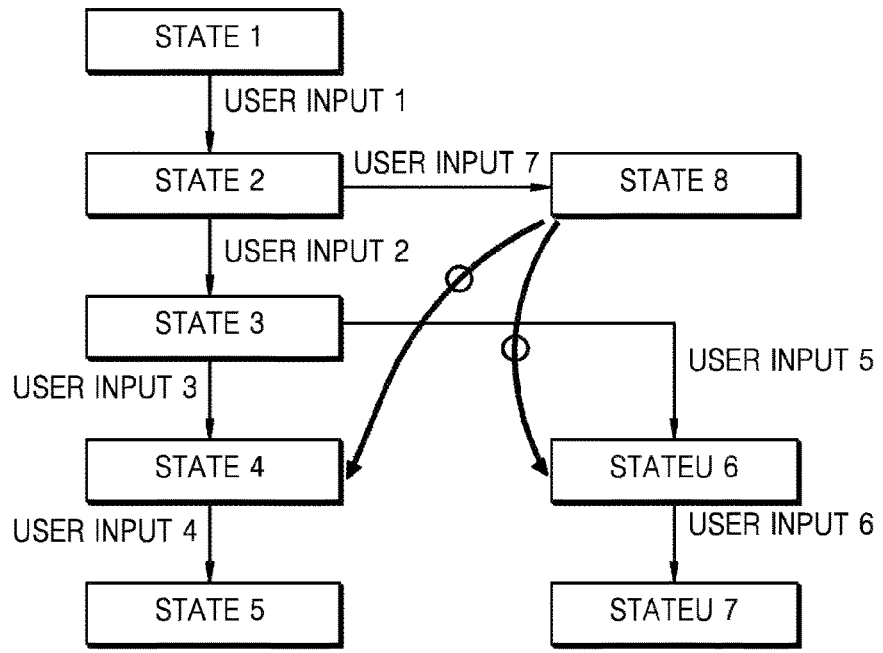

Meanwhile, as illustrated in FIG. 10A, after modifying an operating state thereof from "state 7" to "state 2" based on "recovery input 2," the medical diagnostic apparatus 100 may receive "user input 7" as illustrated in FIG. 10B. The medical diagnostic apparatus 100 may modify an operating state thereof from "state 2" to "state 8" based on "user input 7." The medical diagnostic apparatus 100 may store a history of an operating state corresponding to "user input 7" (that is, state 8).

When storing a history of an operating state corresponding to "user input 7," the medical diagnostic apparatus 100 may renew a history such that "state 8" is included as a subnode of "state 2" in addition to "state 3" and "state 7." That is, according to a storage method based on a tree structure, the medical diagnostic apparatus 100 does not remove "state 3" through "state 7" while storing "state 8." Accordingly, as illustrated in FIG. 10B, the medical diagnostic apparatus 100 may modify an operating state thereof from "state 8" to "state 4" or "state 6" based on a received recovery input.

As described above, the medical diagnostic apparatus 100 according to the current embodiment of the present invention may store a history of operating states based on a tree structure. The medical diagnostic apparatus 100 may display a history stored based on a tree structure as a folder image. The history displayed on the screen of the medical diagnostic apparatus 100 may include icons corresponding to operating states included in the history and icons corresponding to operating states which are subnodes in a folder corresponding to a predetermined operating state which is an upper node.

For example, the medical diagnostic apparatus 100 having an operating state corresponding to FIG. 10B may display a history such that folders respectively corresponding to "state 3" and "state 8" are included in a folder corresponding to "state 2." Also, the medical diagnostic apparatus 100 having an operating state corresponding to FIG. 10B may display "state 4" and "state 6" to be included in a folder corresponding to "state 3."

Meanwhile, referring to FIG. 10B, in the history, "state 5," "state 7," and "state 8" are determined as lowermost subnodes. Accordingly, an icon corresponding to "state 5" is included in a folder corresponding to "state 4," and that "state 5" does not have a subnode may be displayed on the screen. In a folder corresponding to "state 6", an icon corresponding to "state 7" is included, and that "state 7" does not have a subnode may be displayed on the screen. In a folder corresponding to "state 2", an icon corresponding to "state 8" may be included, and that "state 8" does not have a subnode may be displayed on the screen.

Meanwhile, the medical diagnostic apparatus 100 according to the current embodiment of the present invention may be classified as an ultrasound diagnostic apparatus, an X-ray imaging device, a computed tomography (CT) imaging device, and an magnetic resonance (MR) imaging device according to a medical image each apparatus supports.

In particular, an ultrasound diagnostic apparatus is non-invasive and non-destructive, and is thus widely used in the medical field for obtaining information about the inside of an object. An ultrasound diagnostic apparatus is capable of providing a high resolution image of an inside of an object without a surgical operation whereby the object is immediately cut to be observed, and is thus used in the medical field with high importance.

An ultrasound diagnostic apparatus transmits an ultrasound signal to an object while a probe is in contact with a surface of the object, and receives an ultrasound signal reflected by the object (hereinafter referred to as an echo signal). An ultrasound system forms an ultrasound image of the object based on the echo signal received by using the probe, and displays the ultrasound image by using a display unit.

For example, an ultrasound diagnostic apparatus may form and display a B (brightness) mode image on which an intensity of an echo signal reflected from an object is expressed in brightness or a D (Doppler) image on which a Doppler component extracted from an echo signal is expressed in a color or a waveform.

Figure 11:
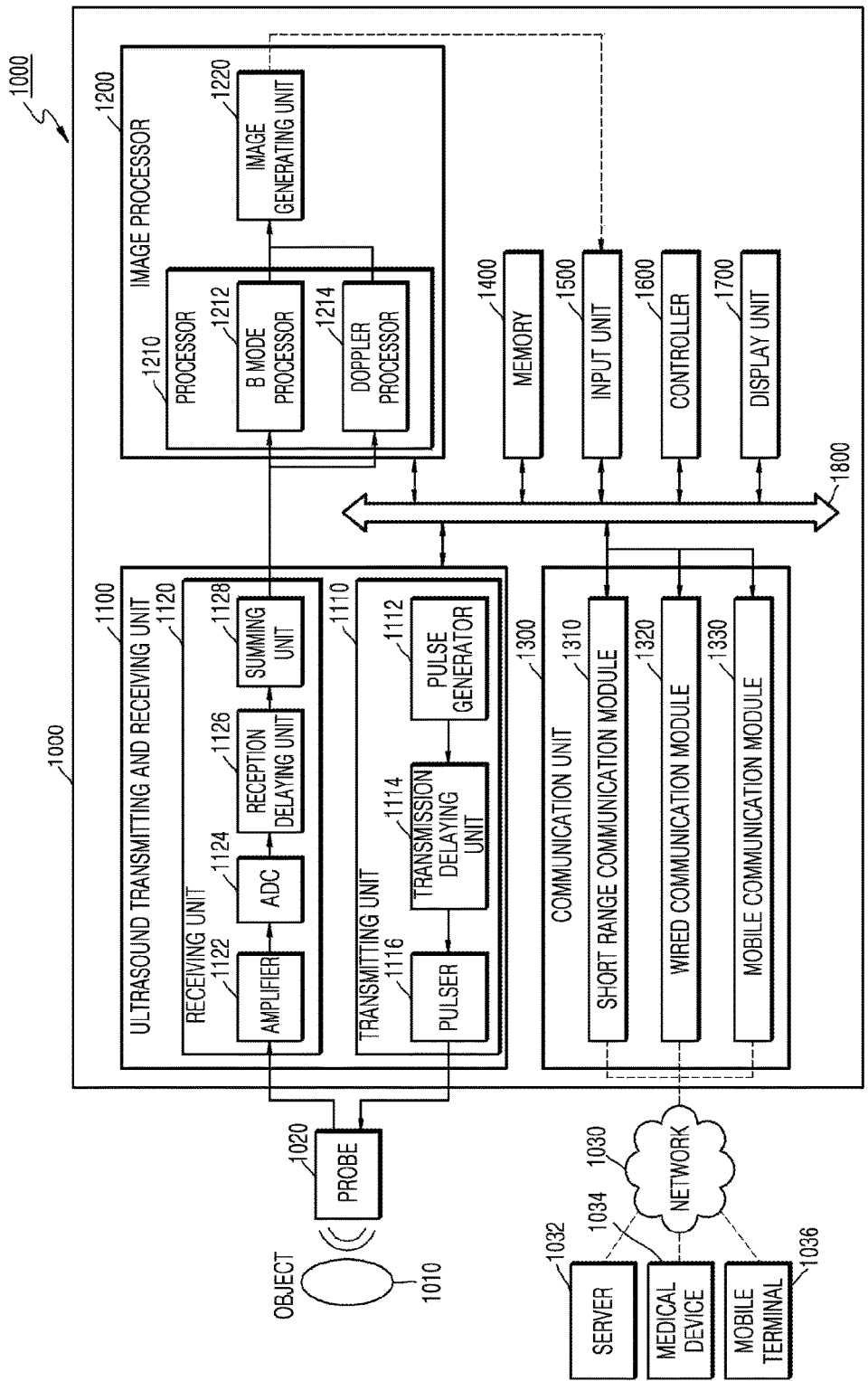
FIG. 11 is a block diagram illustrating an ultrasound diagnostic apparatus to which a medical diagnostic apparatus according to an embodiment of the present invention may be applied.

FIG. 11 is a block diagram illustrating an ultrasound diagnostic apparatus 1000 to which a medical diagnostic apparatus according to an embodiment of the present invention may be applied.

The method of operating the medical diagnostic apparatus 100 according to the current embodiment of the present invention may be performed by using the ultrasound diagnostic apparatus 1000 illustrated in FIG. 10, and the medical diagnostic apparatus 100 may be included in the ultrasound diagnostic apparatus 1000 illustrated in FIG. 10.

The medical diagnostic apparatus 100 of FIG. 1 may perform some or all of functions that are performed by using the ultrasound diagnostic apparatus 1000 of FIG. 10. The display unit 110 of FIG. 1 may correspond to a display unit 1700 of FIG. 10, and the user input unit 120 of FIG. 1 may correspond to an input unit 1500 of FIG. 10, and the storage unit 130 of FIG. 1 may correspond to a memory 1400 of FIG. 10. Also, the controller 140 of FIG. 1 may include some components or functions of an ultrasound transmitting and receiving unit 1100, an image processor 1200, a communication unit 1300, and a controller 1600 of FIG. 10.

The ultrasound diagnostic apparatus 1000 according to the current embodiment of the present invention may include a probe 1020, the ultrasound transmitting and receiving unit 1100, the image processor 1200, the communication unit 1300, the memory 1400, the input unit 1500, and the controller 1600, and these components may be connected to one another via a bus 700.

The transmitting unit 1110 supplies a driving signal to the probe 1020, and includes a pulse generator 1112, a transmission delay unit 1114, and a pulser 1116. The pulse generator 1112 generates a pulse for forming a transmission ultrasound according to a predetermined pulse repetition frequency (PRF), and the transmission delay unit 1114 applies a delay time for determining a transmission directionality to a pulse. Each pulse to which a delay time is applied corresponds to each of a plurality of piezoelectric vibrators included in the probe 1020. The pulser 1116 applies a driving signal (or a driving pulse) to the probe 1020 at a timing corresponding to respective pulses to which a delay time is applied.

The receiving unit 1120 processes an echo signal received from the probe 1020 to generate ultrasound data, and may include an amplifier 1122, an analog digital converter (ADC) 1124, a reception delay unit 1126, and a summing unit 1128. The amplifier 1122 amplifies an echo signal for each channel, and the ADC 1124 converts the amplified echo signal from analog to digital or vice versa. The reception delay unit 1126 applies a delay time for determining reception directionality, to the echo signal which is obtained by digital conversion, and the summing unit 1128 sums up the echo signals that are processed by using the reception delay unit 1126 to generate ultrasound data.

The image processor 1200 generates an ultrasound image through a scan conversion process with respect to ultrasound data generated by using the ultrasound transmitting and receiving unit 1100 and displays the ultrasound image.

A B mode processor 1212 in a data processor 1210 extracts a B mode component from ultrasound data and processes the same. An image generating unit 1220 may generate an ultrasound image whose signal intensity is expressed as brightness, based on the B mode component that is extracted by using the B mode processor 1212.

Likewise, a Doppler processor 1214 in the data processor 1210 may extract a Doppler component from ultrasound data, and the image generating unit 1220 may generate a Doppler image in which motion of an object is expressed in color or waveform based on the extracted Doppler element.

The image generating unit 1220 may generate a 3D ultrasound image by using a volume rendering process with respect to volume data, and may also generate an elastic image which expresses a degree of deformation of the object 1010 according to a pressure as an image. Furthermore, the image generating unit 1220 may express various additional information as text or graphics on the ultrasound image. Meanwhile, the ultrasound image may be stored in the memory 1400.

The communication unit 1300 is connected to a network 1030 in a wired or wireless manner to perform communication with an external device or a server. The communication unit 1300 may exchange data with a hospital server or other medical device in a hospital, which are connected through a Picture Archiving and Communication System (PACS). Also, the communication unit 1300 may perform data communication according to Digital Imaging and Communications in Medicine (DICOM).

The communication unit 1300 may transmit or receive data related to diagnosis of an object such as an ultrasound image or ultrasound data of an object, and may also transmit or receive a medical image captured by using other medical devices such as CT, MRI, or X-ray. Furthermore, the communication unit 1300 may receive information about a diagnosis history or a treatment schedule of a patient from a server and use the information in diagnosis of an object. Moreover, the communication unit 1300 may perform data communication with not only a server or a medical device in a hospital but with a mobile terminal of a doctor or a patient.

The communication unit 1300 may be connected to the network 1030 in a wired or wireless manner to transmit or receive data to or from a server 1032, a medical device 1034, or a mobile terminal 1036. The communication unit 1300 may include at least one component that allows communication with an external device, and may include, for example, a short range communication module 1310, a wired communication module 1320, and a mobile communication module 1330.

The short range communication module 1310 refers to a module for short range communication within a predetermined distance. Examples of short range communication according to an embodiment of the present invention include, without limitation, Wireless LAN, Wi-Fi, Bluetooth, Zigbee, Wi-Fi Direct (WFD), Ultra Wideband (UWB), Infrared Data Association (IrDA), Bluetooth Low Energy (BLE), and Near Field Communication (NFC).

The wired communication module 1320 refers to a module for communication by using an electrical signal or an optical signal. Examples of wired communication technology include using a pair cable, a coaxial cable, an optical fiber cable, or an Ethernet cable.

The mobile communication module 1330 transmits or receives a wireless signal to or from at least one selected from the group consisting of a base station, an external terminal, or a server on a mobile communication network. A wireless signal may include a sound call signal, a video conference call signal, or various types of data according to text or multimedia message transmission and reception.

The memory 1400 stores various information that is processed in the ultrasound diagnostic apparatus 1000. For example, the memory 1400 may store medical data related to diagnosis of an object, such as input or output ultrasound data or an ultrasound image, and may also store an algorithm or a program executed in the ultrasound diagnostic apparatus 1000.

The memory 1400 may be implemented in various types of storage media such as a flash memory, a hard disk, or an electrically erasable programmable read-only memory (EEPROM). Also, the ultrasound diagnostic apparatus 1000 may also operate a web storage or a cloud server that performs a function of the memory 1400 on a web.

The input unit 1500 refers to a unit that receives data for controlling the ultrasound diagnostic apparatus 1000 from a user. Examples of the input unit 1500 include, without limitation, a key pad, a mouse, a touch panel, a touch screen, a track ball, and a jog switch, and may further include various input units such as an electrocardiogram measurement module, a respiration measurement module, a sound recognition sensor, a gesture recognition sensor, a fingerprint recognition sensor, an iris recognition sensor, a depth sensor, or a distance sensor.

The controller 1600 controls the overall operation of the ultrasound diagnostic apparatus 1000. That is, the controller 1600 may control operations to be performed among the probe 1020, the ultrasound transmitting and receiving unit 1100, the image processor 1200, the communication unit 1300, the memory 1400, and the input unit 1500 illustrated in FIG. 11.

Some or all of the probe 1020, the ultrasound transmitting and receiving unit 1100, the image processor 1200, the communication unit 1300, the memory 1400, the input unit 1500, and the controller 1600 may be operated via a software module but are not limited thereto, and some of the above components may also operate via hardware. In addition, at least some of the ultrasound transmitting and receiving unit 1100, the image processor 1200, and the communication unit 1300 may be included in the controller 1600, but the ultrasound diagnostic apparatus 1000 is not limited to the above implementation structure.

An embodiment of the present invention may also be realized in a form of a recording medium including commands executable by a computer, such as a program module executed by a computer. A computer-readable recording medium may be an arbitrary available medium accessible by a computer, and may be any one of volatile, nonvolatile, separable, and non-separable media. Also, examples of the computer-readable recording medium may include a computer storage medium and a communication medium. Examples of the computer storage medium include volatile, nonvolatile, separable, and non-separable media realized by an arbitrary method or technology for storing information about a computer-readable command, a data structure, a program module, or other data. The communication medium may include a computer-readable command, a data structure, a program module, other data of a modulated data signal, such as carrier waves, or other transmission mechanisms, and may be an arbitrary information transmission medium.

While this invention has been particularly shown and described with reference to embodiments thereof, it will be understood by those of ordinary skill in the art that various changes in form and details may be made therein without departing from the spirit and scope of the invention as defined by the appended claims. The embodiments should be considered in a descriptive sense only and not for purposes of limitation. For example, each element described as a single type may be distributed, and similarly, elements described to be distributed may be combined.

The scope of the invention is defined not by the detailed description of the invention but by the appended claims, and all differences within the scope will be construed as being included in the present invention.

What is claimed is:

1. A method of operating a medical diagnostic apparatus that displays a medical image, the method comprising:
    modifying, by a processor, an operating state of the medical diagnostic apparatus from a first state to a second state based on sequential first user inputs, wherein the first state is determined as an upper node, and the second state is determined as a subnode of the first state;
    storing, by a memory, a history of a plurality of operating states respectively corresponding to the first user inputs, based on a tree structure formed of at least one upper node and at least one subnode;
    displaying, on a display, the history based on the tree structure as a folder image including at least one icon corresponding to the at least one upper node and at least one icon corresponding to the at least one subnode, wherein the second state indicating a current state and a parameter value used for modifying from the first state to the second state are highlighted in the history;
    receiving, by a control panel, a first recovery input to return to a previous operating state included in the history, based on the tree structure;

selecting, by the processor, a third state corresponding to the previous operating state from among the plurality of operating states included in the history, based on the first recovery input;

modifying, by the processor, the operating state of the medical diagnostic apparatus from the second state to the third state;

displaying, on the display, at least one medical image corresponding to the third state of the medical diagnostic apparatus;

receiving, by the control panel, a second user input;

modifying, by the processor, an operating state of the medical diagnostic apparatus from the third state to a fourth state based on the second user input;

renewing, by the processor, the history such that the fourth state is further included as a subnode of the third state based on the tree structure and storing the renewed history; and modifying, by the processor, an operating state of the medical diagnostic apparatus based on a second recovery input, from the fourth state to the second state included in the renewed history.

2. The method of claim 1, wherein the modifying the operating state of the medical diagnostic apparatus from the first state to the second state comprises modifying a displaying method of displaying the at least one medical image or modifying a parameter applied to the at least one medical image.

3. The method of claim 1, wherein the modifying of an operating state of the medical diagnostic apparatus from the first state to the second state comprises modifying an ultrasound mode of the displayed at least one medical image, modifying the number of medical images displayed on a single screen, and modifying a 2D medical image to a 3D medical image or from a 3D medical image to a 2D medical image.

4. The method of claim 1, wherein the storing of a history comprises: selecting at least one user input related to modification of an operating state of the medical diagnostic apparatus from among the first user inputs; and storing the operating state corresponding to the selected first user input as the history.

5. The method of claim 1, wherein the selecting of the third state comprises selecting an operating state just before the second state.

6. The method of claim 1, wherein the selecting of the third state comprises selecting the third state from among the plurality of operating states based on a number of input or duration time of the first recovery input.

7. The method of claim 1, wherein the receiving of the first recovery input comprises receiving an input via which the third state from among the operating states is selected, with respect to the displayed history.

8. The method of claim 1, wherein the modifying of an operating state of the medical diagnostic apparatus from the first state to the second state comprises modifying a parameter applied to the at least one medical image based on the first user inputs, from a first value to a second value, and wherein the selecting of the third state comprises selecting an operating state that returns from the second value to the first value by a predetermined value that is determined based on a user set up.

9. The method of claim 1, wherein the storing of the history comprises storing the history in a form that an external device uses to modify an operating state of the external device.

10. The method of claim 1, further comprising: receiving, by the control panel, a selection at least two of the plurality of operating states included in the history; and repeatedly, by processor, performing operations within the history such that the medical diagnostic apparatus is repeatedly modified from one operating state to another operating state based on the at least two of the plurality of operating states.

11. A medical diagnostic apparatus comprising:

a display that displays a medical image based on an operating state of the medical diagnostic apparatus;

a control panel that receives sequential first user inputs and a first recovery input;

a memory that stores a history of a plurality of operating states respectively corresponding to the first user inputs, based on a tree structure formed of at least one upper node and at least one subnode; and a processor that modifies the operating state of the medical diagnostic apparatus from a first state to a second state based on the first user inputs, wherein the first state is determined as an upper node, and the second state is determined as a subnode of the first state, controls the display to display the history based on the tree structure as a folder image including at least one icon corresponding to the at least one upper node and at least one icon corresponding to the at least one subnode, wherein the second state indicating a current state and a parameter value used for modifying from the first state to the second state are highlighted in the history, selects, based on the first recovery input to return to a previous operating state included in the history, based on the tree structure, a third state corresponding to the previous operating state from among the plurality of operating states included in the history, modifies the operating state of the medical diagnostic apparatus from the second state to the third state, and controls the display to display at least one medical image corresponding to the third state of the medical diagnostic apparatus, wherein the control panel further receives a second user input, wherein the processor modifies an operating state of the medical diagnostic apparatus from the third state to a fourth state based on the second user input, wherein the memory renews the history such that the fourth state is further included as a subnode of the third state based on the tree structure and stores the renewed history, and wherein the processor modifies an operating state of the medical diagnostic apparatus based on a second recovery input, from the fourth state to the second state included in the renewed history.

12. The medical diagnostic apparatus of claim 11, wherein the processor modifies the operating state of the medical diagnostic apparatus from the first state to the second state by modifying a displaying method of displaying the at least one medical image or by modifying a parameter applied to the at least one medical image.

13. The medical diagnostic apparatus of claim 11, wherein the processor modifies the operating state of the medical diagnostic apparatus from the first state to the second state by modifying an ultrasound mode of the displayed at least one medical image, by modifying the number of medical images displayed on a single screen, or by modifying the at least one medical image from a 2D mode to a 3D mode or from a 3D mode to a 2D mode.

14. The medical diagnostic apparatus of claim 11, wherein the processor selects at least one of the first user inputs, which is related to modification of an operating state of the medical diagnostic apparatus, and
wherein the memory stores the operating state corresponding to the selected at least one first user input as the history.

15. The medical diagnostic apparatus of claim 11, wherein the processor selects an operating state just before the second state as the third state.

16. The medical diagnostic apparatus of claim 11, wherein the processor selects the third state from among the plurality of operating states based on a number of input or a duration time of the first recovery input.

17. The medical diagnostic apparatus of claim 11, wherein the control panel receives an input via which the third state is selected from among the operating states, with respect to the displayed history.

18. The medical diagnostic apparatus of claim 11, wherein the processor modifies the operating state of the medical diagnostic apparatus from the first state to the second state by modifying a parameter applied to the at least one medical image based on the first user inputs, from a first value to a second value, and selects, as the third state, an operating state that returns from the second value to the first value by a predetermined value that is determined based on a user set up.

19. The medical diagnostic apparatus of claim 11, wherein the memory stores the history in a form that an external device uses to modify an operating state of the external device.

20. A non-transitory computer readable recording medium having recorded thereon instructions that when executed by a processor, cause the processor to perform:
modifying an operating state of a medical diagnostic apparatus from a first state to a second state based on sequential first user inputs, wherein the first state is determined as an upper node, and the second state is determined as a subnode of the first state;
controlling a memory to store a history of a plurality of operating states respectively corresponding to the first user inputs, based on a tree structure formed of at least one upper node and at least one subnode;
controlling a display to display the history based on the tree structure as a folder image including at least one icon corresponding to the at least one upper node and at least one icon corresponding to the at least one subnode, wherein the second state indicating a current state and a parameter value used for modifying from the first state to the second state are highlighted in the history;
controlling a control panel to receive a first recovery input to return to a previous operating state included in the history, based on the tree structure;
selecting a third state corresponding to the previous operating state from among the plurality of operating states included in the history, based on the first recovery input;
modifying the operating state of the medical diagnostic apparatus from the second state to the third state;
controlling the display to display at least one medical image corresponding to the third state of the medical diagnostic apparatus;
controlling the control panel to receive a second user input; modifying an operating state of the medical diagnostic apparatus from the third state to a fourth state based on the second user input;
renewing the history such that the fourth state is further included as a subnode of the third state based on the tree structure and storing the renewed history; and
modifying an operating state of the medical diagnostic apparatus based on a second recovery input, from the fourth state to the second state included in the renewed history.

* * * * *